(12) United States Patent
Bardy

(10) Patent No.: US 6,261,230 B1
(45) Date of Patent: Jul. 17, 2001

(54) SYSTEM AND METHOD FOR PROVIDING NORMALIZED VOICE FEEDBACK FROM AN INDIVIDUAL PATIENT IN AN AUTOMATED COLLECTION AND ANALYSIS PATIENT CARE SYSTEM

(75) Inventor: Gust H. Bardy, Seattle, WA (US)

(73) Assignee: Cardiac Intelligence Corporation, Seattle, WA (US)

( * ) Notice: Subject to any disclaimer, the term of this patent is extended or adjusted under 35 U.S.C. 154(b) by 0 days.

(21) Appl. No.: 09/476,600

(22) Filed: Dec. 31, 1999

Related U.S. Application Data

(63) Continuation-in-part of application No. 09/361,777, filed on Jul. 26, 1999, which is a continuation-in-part of application No. 09/324,894, filed on Jun. 3, 1999.

(51) Int. Cl.[7] .................................................. A61B 10/00
(52) U.S. Cl. ............................................................ 600/300
(58) Field of Search ........................... 600/300; 128/904, 128/906, 920

(56) References Cited

U.S. PATENT DOCUMENTS

| | | | |
|---|---|---|---|
| 4,987,897 | 1/1991 | Funke | 128/419 |
| 5,040,536 | 8/1991 | Riff | 128/419 |
| 5,113,859 | 5/1992 | Funke | 128/419 |
| 5,113,869 | 5/1992 | Nappholz et al. | 128/696 |
| 5,331,549 | 7/1994 | Crawford, Jr. . | |
| 5,336,245 | 8/1994 | Adams et al. | 607/32 |
| 5,357,427 * | 10/1994 | Langen et al. | 364/413.02 |
| 5,390,238 | 2/1995 | Kirk et al. . | |
| 5,544,661 * | 8/1996 | Davis et al. | 128/700 |
| 5,553,609 * | 9/1996 | Chen et al. | 128/630 |
| 5,704,366 | 1/1998 | Tacklind et al. . | |
| 5,711,297 * | 1/1998 | Iliff | 128/630 |
| 5,713,350 | 2/1998 | Yokota et al. . | |
| 5,752,976 | 5/1998 | Duffin et al. | 607/32 |
| 5,778,882 | 7/1998 | Raymond et al. . | |
| 5,855,593 | 1/1999 | Olson et al. | 607/9 |
| 5,876,353 | 3/1999 | Riff | 600/547 |
| 5,931,857 | 8/1999 | Prieve et al. | 607/14 |
| 5,987,352 | 11/1999 | Klein et al. | 600/509 |

* cited by examiner

Primary Examiner—William E. Kamm
(74) Attorney, Agent, or Firm—Patrick J.S. Inouye

(57) ABSTRACT

A system and a method for providing normalized voice feedback from an individual patient in an automated collection and analysis patient care system are described. A set of collected measures retrieved on a substantially regular basis is periodically received from a medical device having a sensor for monitoring at least one physiological measure of an individual patient. The collected measures set includes individual measures which each relate to patient information recorded by the medical device. The collected measures set are stored into a patient care record for the individual patient within a database. The database is organized to store one or more patient care records which each include a plurality of the collected measures sets. Voice feedback is spoken by the individual patient into a remote client substantially contemporaneous to the collection of an identifiable device measures set. The voice feedback is processed into a set of quality of life measures which each relate to patient self-assessment indicators. The identified collected device measures set and the quality of life measures set are received and stored into the patient care record for the individual patient within the database. The identified collected device measures set, the quality of life measures set, and one or more of the collected device measures sets in the patient care record for the individual patient are analyzed relative to one or more other collected device measures sets stored in the database server to determine a patient status indicator.

32 Claims, 29 Drawing Sheets

Figure 5.

| 71 | 72 | 73 | 74 | 75 | 76 | 77 | 78 | 79 | 80 | 81 | 82 |
|---|---|---|---|---|---|---|---|---|---|---|---|
| Atrial Electrical Activity | Ventricular Electrical Activity | Time of Day | Activity Level | Cardiac Output | Oxygen Level | Cardio-vascular Pressure Measures | Pulmonary Pressure Measures | Interventions Made | Success of Interventions Made | Battery Status | Program Settings |

Patient 1

| Set 0 | | | | Set n-2 | Set n-1 | Set n |
|---|---|---|---|---|---|---|
| $X_0$ | • | • | • | $X_{n-2}$ | $X_{n-1}$ | $X_n$ |
| $Y_0$ | • | • | • | $Y_{n-2}$ | $Y_{n-1}$ | $Y_n$ |
| $Z_0$ | • | • | • | $Z_{n-2}$ | $Z_{n-1}$ | $Z_n$ |

*time* →

Patient 2

| Set 0 | | | | Set n-2 | Set n-1 | Set n |
|---|---|---|---|---|---|---|
| $X_{0'}$ | • | • | • | $X_{n-2'}$ | $X_{n-1'}$ | $X_{n'}$ |
| $Y_{0'}$ | • | • | • | $Y_{n-2'}$ | $Y_{n-1'}$ | $Y_{n'}$ |
| $Z_{0'}$ | • | • | • | $Z_{n-2'}$ | $Z_{n-1'}$ | $Z_{n'}$ |

*time* →

Patient 3

| Set 0 | | | | Set n-2 | Set n-1 | Set n |
|---|---|---|---|---|---|---|
| $X_{0''}$ | • | • | • | $X_{n-2''}$ | $X_{n-1''}$ | $X_{n''}$ |
| $Y_{0''}$ | • | • | • | $Y_{n-2''}$ | $Y_{n-1''}$ | $Y_{n''}$ |
| $Z_{0''}$ | • | • | • | $Z_{n-2''}$ | $Z_{n-1''}$ | $Z_{n''}$ |

*time* →

Figure 24.

Patient 1

| | Set 0 | | • | • | • | Set n-2 | Set n-1 | Set n |
|---|---|---|---|---|---|---|---|---|
| Site A | $X_{0_A}$ | | • | • | • | $X_{n-2_A}$ | $X_{n-1_A}$ | $X_{n_A}$ |
| | $Y_{0_A}$ | | • | • | • | $Y_{n-2_A}$ | $Y_{n-1_A}$ | $Y_{n_A}$ |
| | $Z_{0_A}$ | | • | • | • | $Z_{n-2_A}$ | $Z_{n-1_A}$ | $Z_{n_A}$ |
| Site B | $X_{0_B}$ | | • | • | • | $X_{n-2_B}$ | $X_{n-1_B}$ | $X_{n_B}$ |
| | $Y_{0_B}$ | | • | • | • | $Y_{n-2_B}$ | $Y_{n-1_B}$ | $Y_{n_B}$ |
| | $Z_{0_B}$ | | • | • | • | $Z_{n-2_B}$ | $Z_{n-1_B}$ | $Z_{n_B}$ |
| Site C | $X_{0_C}$ | | • | • | • | $X_{n-2_C}$ | $X_{n-1_C}$ | $X_{n_C}$ |
| | $Y_{0_C}$ | | • | • | • | $Y_{n-2_C}$ | $Y_{n-1_C}$ | $Y_{n_C}$ |
| | $Z_{0_C}$ | | • | • | • | $Z_{n-2_C}$ | $Z_{n-1_C}$ | $Z_{n_C}$ | time →

Patient 2

| | Set 0 | | • | • | • | Set n-2 | Set n-1 | Set n |
|---|---|---|---|---|---|---|---|---|
| Site A | $X'_{0_A}$ | | • | • | • | $X'_{n-2_A}$ | $X'_{n-1_A}$ | $X'_{n_A}$ |
| | $Y'_{0_A}$ | | • | • | • | $Y'_{n-2_A}$ | $Y'_{n-1_A}$ | $Y'_{n_A}$ |
| | $Z'_{0_A}$ | | • | • | • | $Z'_{n-2_A}$ | $Z'_{n-1_A}$ | $Z'_{n_A}$ |
| Site B | $X'_{0_B}$ | | • | • | • | $X'_{n-2_B}$ | $X'_{n-1_B}$ | $X'_{n_B}$ |
| | $Y'_{0_B}$ | | • | • | • | $Y'_{n-2_B}$ | $Y'_{n-1_B}$ | $Y'_{n_B}$ |
| | $Z'_{0_B}$ | | • | • | • | $Z'_{n-2_B}$ | $Z'_{n-1_B}$ | $Z'_{n_B}$ | time →

Patient 3

| | Set 0 | | • | • | • | Set n-2 | Set n-1 | Set n |
|---|---|---|---|---|---|---|---|---|
| Site A | $X''_{0_A}$ | | • | • | • | $X''_{n-2_A}$ | $X''_{n-1_A}$ | $X''_{n_A}$ |
| | $Y''_{0_A}$ | | • | • | • | $Y''_{n-2_A}$ | $Y''_{n-1_A}$ | $Y''_{n_A}$ |
| | $Z''_{0_A}$ | | • | • | • | $Z''_{n-2_A}$ | $Z''_{n-1_A}$ | $Z''_{n_A}$ |
| Site D | $X''_{0_D}$ | | • | • | • | $X''_{n-2_D}$ | $X''_{n-1_D}$ | $X''_{n_D}$ |
| | $Y''_{0_D}$ | | • | • | • | $Y''_{n-2_D}$ | $Y''_{n-1_D}$ | $Y''_{n_D}$ |
| | $Z''_{0_D}$ | | • | • | • | $Z''_{n-2_D}$ | $Z''_{n-1_D}$ | $Z''_{n_D}$ | time →

SYSTEM AND METHOD FOR PROVIDING NORMALIZED VOICE FEEDBACK FROM AN INDIVIDUAL PATIENT IN AN AUTOMATED COLLECTION AND ANALYSIS PATIENT CARE SYSTEM

CROSS-REFERENCE TO RELATED APPLICATION

This patent application is a continuation-in-part of commonly owned U.S. patent application, Ser. No. 09/361,777, filed Jul. 26, 1999, pending, which is a continuation-in-part of commonly owned U.S. patent application, Ser. No. 09/324,894, pending, filed Jun. 3, 1999, the disclosures of which are incorporated herein by reference.

FIELD OF THE INVENTION

The present invention relates in general to automated data collection and analysis, and, in particular, to a system and method for providing normalized voice feedback from an individual patient in an automated collection and analysis patient care system.

BACKGROUND OF THE INVENTION

A broad class of medical subspecialties, including cardiology, endocrinology, hematology, neurology, gastroenterology, urology, ophthalmology, and otolaryngology, to name a few, rely on accurate and timely patient information for use in aiding health care providers in diagnosing and treating diseases and disorders. Often, proper medical diagnosis requires information on physiological events of short duration and sudden onset, yet these types of events are often occur infrequently and with little or no warning. Fortunately, such patient information can be obtained via external, implantable, cutaneous, subcutaneous, and manual medical devices, and combinations thereof. For example, in the area of cardiology, implantable pulse generators (IPGs) are medical devices commonly used to treat irregular heartbeats, known as arrhythmias. There are three basic types of IPGs. Cardiac pacemakers are used to manage bradycardia, an abnormally slow or irregular heartbeat. Bradycardia can cause symptoms such as fatigue, dizziness, and fainting. Implantable cardioverter defibrillators (ICDs) are used to treat tachycardia, heart rhythms that are abnormally fast and life threatening. Tachycardia can result in sudden cardiac death (SCD). Finally, implantable cardiovascular monitors and therapeutic devices are used to monitor and treat structural problems of the heart, such as congestive heart failure, as well as rhythm problems.

Pacemakers and ICDs, as well as other types of implantable and external medical devices, are equipped with an on-board, volatile memory in which telemetered signals can be stored for later retrieval and analysis. In addition, a growing class of cardiac medical devices, including implantable heart failure monitors, implantable event monitors, cardiovascular monitors, and therapy devices, are being used to provide similar stored device information. These devices are able to store more than thirty minutes of per heartbeat data. Typically, the telemetered signals can provide patient device information recorded on a per heartbeat, binned average basis, or derived basis from, for example, minute ventilation, patient activity score, cardiac output score, mixed venous oxygen score, cardiovascular pressure measures, time of day, and any interventions and the relative success of such interventions. In addition, many such devices can have multiple sensors, or several devices can work together, for monitoring different sites within a patient's body.

Presently, stored device information is retrieved using a proprietary interrogator or programmer, often during a clinic visit or following a device event. The volume of data retrieved from a single device interrogation "snapshot" can be large and proper interpretation and analysis can require significant physician time and detailed subspecialty knowledge, particularly by cardiologists and cardiac electrophysiologists. The sequential logging and analysis of regularly scheduled interrogations can create an opportunity for recognizing subtle and incremental changes in patient condition otherwise undetectable by inspection of a single "snapshot." However, present approaches to data interpretation and understanding and practical limitations on time and physician availability make such analysis impracticable.

Similarly, the determination and analysis of the quality of life issues which typically accompany the onset of a chronic yet stable diseases, such as coronaryartery disease, is a crucial adjunct to assessing patient wellness and progress. However, unlike in a traditional clinical setting, physicians participating in providing remote patient care are not able to interact with their patients in person. Consequently, quality of life measures, such as how the patient subjectively looks and feels, whether the patient has shortness of breath, can work, can sleep, is depressed, is sexually active, can perform activities of daily life, and so on, cannot be implicitly gathered and evaluated.

A prior art system for collecting and analyzing pacemaker and ICD telemetered signals in a clinical or office setting is the Model 9790 Programmer, manufactured by Medtronic, Inc., Minneapolis, Minn. This programmer can be used to retrieve data, such as patient electrocardiogram and any measured physiological conditions, collected by the IPG for recordation, display and printing. The retrieved data is displayed in chronological order and analyzed by a physician. Comparable prior art systems are available from other IPG manufacturers, such as the Model 2901 Programmer Recorder Monitor, manufactured by Guidant Corporation, Indianapolis, Ind., which includes a removable floppy diskette mechanism for patient data storage. These prior art systems lack remote communications facilities and must be operated with the patient present. These systems present a limited analysis of the collected data based on a single device interrogation and lack the capability to recognize trends in the data spanning multiple episodes over time or relative to a disease specific peer group.

A prior art system for locating and communicating with a remote medical device implanted in an ambulatory patient is disclosed in U.S. Pat. No. 5,752,976 ('976). The implanted device includes a telemetry transceiver for communicating data and operating instructions between the implanted device and an external patient communications device. The communications device includes a communication link to a remote medical support network, a global positioning satellite receiver, and a patient activated link for permitting patient initiated communication with the medical support network. Patient voice communications through the patient link include both actual patient voice and manually actuated signaling which may convey an emergency situation. The patient voice is converted to an audio signal, digitized, encoded, and transmitted by data bus to a system controller.

Related prior art systems for remotely communicating with and receiving telemetered signals from a medical device are disclosed in U.S. Pat. Nos. 5,113,869 ('869) and 5,336,245 ('245). In the '869 patent, an implanted AECG monitor can be automatically interrogated at preset times of day to telemeter out accumulated data to a telephonic communicator or a full disclosure recorder. The communicator can be automatically triggered to establish a telephonic communication link and transmit the accumulated data to an office or clinic through a modem. In the '245 patent, telemetered data is downloaded to a larger capacity, external data recorder and is forwarded to a clinic using an autodialer and fax modem operating in a personal computer-based programmer/interrogator. However, the '976 telemetry transceiver, '869 communicator, and '245 programmer/interrogator are limited to facilitating communication and transferal of downloaded patient data and do not include an ability to automatically track, recognize, and analyze trends in the data itself Moreover, the '976 telemetry transceiver facilitates patient voice communications through transmission of a digitized audio signal and does not perform voice recognition or other processing to the patient's voice.

In addition, the uses of multiple sensors situated within a patient's body at multiple sites are disclosed in U.S. Pat. Nos. 5,040,536 ('536) and 5,987,352 ('352). In the '536 patent, an intravascular pressure posture detector includes at least two pressure sensors implanted in different places in the cardiovascular system, such that differences in pressure with changes in posture are differentially measurable. However, the physiological measurements are used locally within the device, or in conjunction with any implantable device, to effect a therapeutic treatment. In the '352 patent, an event monitor can include additional sensors for monitoring and recording physiological signals during arrhythmia and syncopal events. The recorded signals can be used for diagnosis, research or therapeutic study, although no systematic approach to analyzing these signals, particularly with respect to peer and general population groups, is presented.

Thus, there is a need for a system and method for providing continuous retrieval, transferal, and automated analysis of retrieved medical device information, such as telemetered signals, retrieved in general from a broad class of implantable and external medical devices. Preferably, the automated analysis would include recognizing a trend indicating disease onset, progression, regression, and status quo and determining whether medical intervention is necessary.

There is a further need for a system and method that would allow consideration of sets of collected measures, both actual and derived, from multiple device interrogations. These collected measures sets could then be compared and analyzed against short and long term periods of observation.

There is a further need for a system and method that would enable the measures sets for an individual patient to be self-referenced and cross-referenced to similar or dissimilar patients and to the general patient population. Preferably, the historical collected measures sets of an individual patient could be compared and analyzed against those of other patients in general or of a disease specific peer group in particular.

There is a further need for a system and method for accepting and normalizing live voice feedback spoken by an individual patient while an identifiable set of telemetered signals is collected by a implantable medical device. Preferably, the normalized voice feedback a semi-quantitative self-assessment of an individual patient's physical and emotional well being at a time substantially contemporaneous to the collection of the telemetered signals.

SUMMARY OF THE INVENTION

The present invention provides a system and method for automated collection and analysis of patient information retrieved from an implantable medical device for remote patient care. The patient device information relates to individual measures recorded by and retrieved from implantable medical devices, such as IPGs and monitors. The patient device information is received on a regular, e.g., daily, basis as sets of collected measures which are stored along with other patient records in a database. The information can be analyzed in an automated fashion and feedback provided to the patient at any time and in any location.

The present invention also provides a system and method for providing normalized voice feedback from an individual patient in an automated collection and analysis patient care system. As before, patient device information is received on a regular, e.g., daily, basis as sets of collected measures which are stored along with other patient records in a database. Voice feedback spoken by an individual patient is processed into a set of quality of life measures by a remote client substantially contemporaneous to the recordation of an identifiable set of collected device measures by the implantable medical device. The processed voice feedback and identifiable collected device measures set are both received and stored into the patient record in the database for subsequent evaluation.

An embodiment of the present invention is a system and method for providing normalized voice feedback from an individual patient in an automated collection and analysis patient care system. A set of device measures from a medical device adapted to be implanted is collected. The collected device measures set includes individual device measures which each relate to patient information recorded by the medical device adapted to be implanted for the individual patient. The collected device measures set from the medical device adapted to be implanted are periodically received over a communications link which is interfaced to a network server. The collected device measures set are stored into a patient care record for the individual patient within a database server. The database server is organized to store one or more patient care records which each include a plurality of the collected device measures sets. Voice feedback is spoken by the individual patient into a remote client substantially contemporaneous to the collection of an identifiable device measures set. The voice feedback is processed into a set of quality of life measures which each relate to patient self-assessment indicators. The identified collected device measures set and the quality of life measures set are received over the communications link interfaced to the network server respectively from the medical device adapted to be implanted and the remote client. The identified collected device measures set and the quality of life measures set are stored into the patient care record for the individual patient within the database server. The identified collected device measures set, the quality of life measures set, and one or more of the collected device measures sets in the patient care record for the individual patient are analyzed relative to one or more other collected device measures sets stored in the database server to determine a patient status indicator.

A further embodiment of the present invention is a system and method for providing normalized voice feedback from an individual patient in an automated collection and analysis patient care system. A set of collected measures retrieved on a substantially regular basis is periodically received from a medical device having a sensor for monitoring at least one physiological measure of an individual patient. The collected measures set includes individual measures which each relate to patient information recorded by the medical device. The collected measures set are stored into a patient care record for the individual patient within a database. The database is organized to store one or more patient care records which each include a plurality of the collected measures sets. Voice feedback is spoken by the individual patient into a remote client, which can include the medical device itself, whether implantable, external or otherwise, substantially contemporaneous to the collection of an identifiable device measures set. The voice feedback is processed into a set of quality of life measures which each relate to patient self-assessment indicators. The identified collected device measures set and the quality of life measures set are received and stored into the patient care record for the individual patient within the database. The identified collected device measures set, the quality of life measures set, and one or more of the collected device measures sets in the patient care record for the individual patient are analyzed relative to one or more other collected device measures sets stored in the database server to determine a patient status indicator.

The present invention facilitates the gathering, storage, and analysis of critical patient information obtained on a routine basis and analyzed in an automated manner. Thus, the burden on physicians and trained personnel to evaluate the volumes of information is significantly minimized while the benefits to patients are greatly enhanced.

The present invention also enables the simultaneous collection of both physiological measures from implantable medical devices and quality of life measures spoken in the patient's own words. Voice recognition technology enables the spoken patient feedback to be normalized to a standardized set of semi-quantitative quality of life measures, thereby facilitating holistic remote, automated patient care.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 5 is a database schema showing, by way of example, the organization of a cardiac patient care record stored in the database of the system of FIG. 1;

FIG. 6 is a record view showing, by way of example, a set of partial cardiac patient care records stored in the database of the system of FIG. 1;

FIG. 24 is a record view showing, by way of example, a set of partial cardiac patient care records stored in the database of the system of FIG. 21;

DETAILED DESCRIPTION

Figure 1:
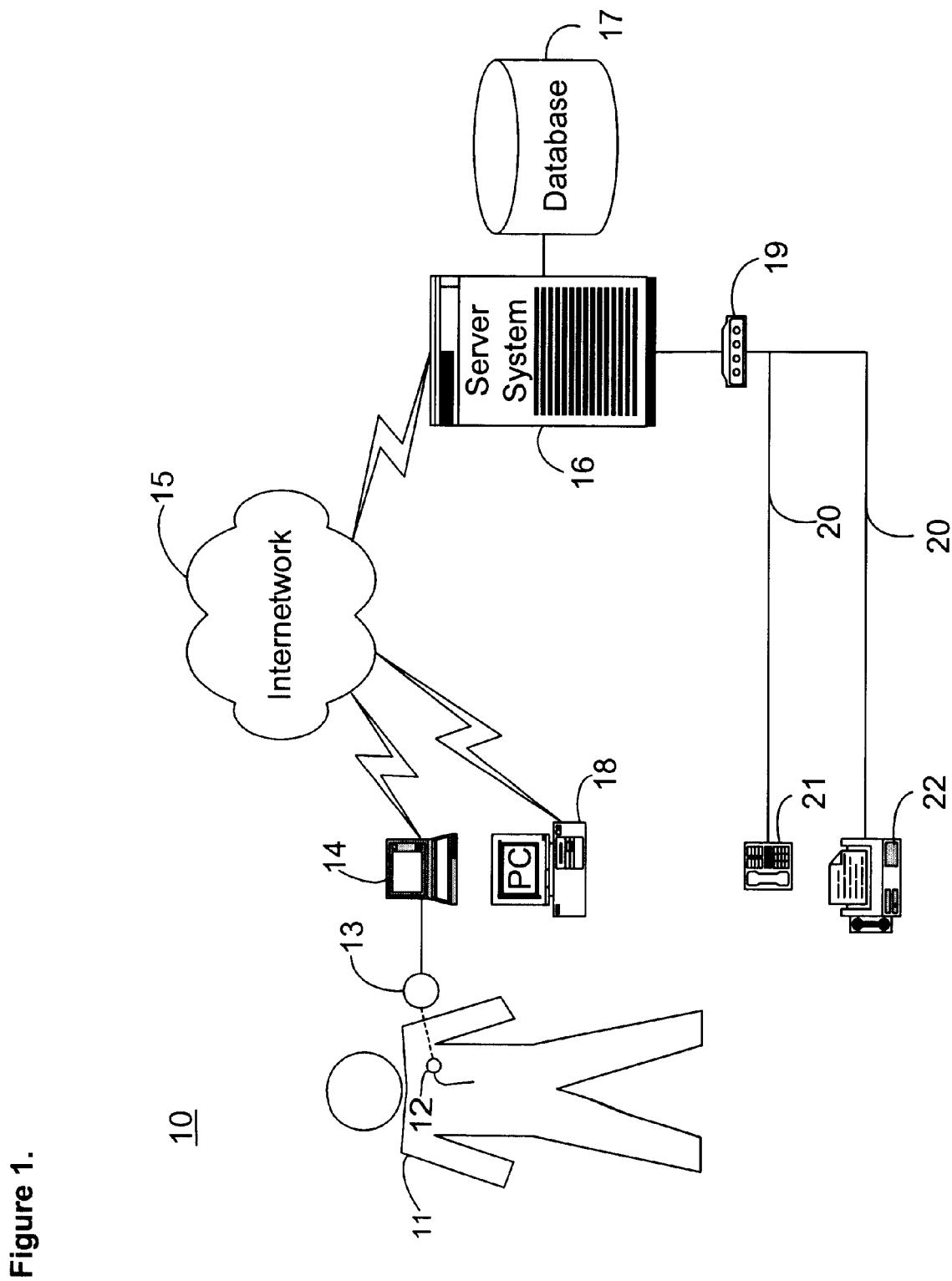
FIG. 1 is a block diagram showing a system for automated collection and analysis of patient information retrieved from an implantable medical device for remote patient care in accordance with the present invention.

FIG. 1 is a block diagram showing a system 10 for automated collection and analysis of patient information retrieved from an implantable medical device for remote patient care in accordance with the present invention. A patient 11 is a recipient of an implantable medical device 12, such as, by way of example, an IPG or a heart failure or event monitor, with a set of leads extending into his or her heart. The implantable medical device 12 includes circuitry for recording into a short-term, volatile memory telemetered signals, which are stored as a set of collected measures for later retrieval.

For an exemplary cardiac implantable medical device, the telemetered signals non-exclusively present patient information recorded on a per heartbeat, binned average or derived basis and relating to: atrial electrical activity, ventricular electrical activity, minute ventilation, patient activity score, cardiac output score, mixed venous oxygenation score, cardiovascular pressure measures, time of day, the number and types of interventions made, and the relative success of any interventions, plus the status of the batteries and programmed settings. Examples of pacemakers suitable for use in the present invention include the Discovery line of pacemakers, manufactured by Guidant Corporation, Indianapolis, Ind. Examples of ICDs suitable for use in the present invention include the Gem line of ICDs, manufactured by Medtronic Corporation, Minneapolis, Minn.

In the described embodiment, the patient 11 has a cardiac implantable medical device. However, a wide range of related implantable medical devices are used in other areas of medicine and a growing number of these devices are also capable of measuring and recording patient information for later retrieval. These implantable medical devices include monitoring and therapeutic devices for use in metabolism, endocrinology, hematology, neurology, muscular disorders, gastroenterology, urology, ophthalmology, otolaryngology, orthopedics, and similar medical subspecialties. One skilled in the art would readily recognize the applicability of the present invention to these related implantable medical devices.

On a regular basis, the telemetered signals stored in the implantable medical device 12 are retrieved. By way of example, a programmer 14 can be used to retrieve the telemetered signals. However, any form of programmer, interrogator, recorder, monitor, or telemetered signals transceiver suitable for communicating with an implantable medical device 12 could be used, as is known in the art. In addition, a personal computer or digital data processor could be interfaced to the implantable medical device 12, either directly or via a telemetered signals transceiver configured to communicate with the implantable medical device 12.

Using the programmer 14, a magnetized reed switch (not shown) within the implantable medical device 12 closes in response to the placement of a wand 13 over the location of the implantable medical device 12. The programmer 14 communicates with the implantable medical device 12 via RF signals exchanged through the wand 13. Programming or interrogating instructions are sent to the implantable medical device 12 and the stored telemetered signals are downloaded into the programmer 14. Once downloaded, the telemetered signals are sent via an internetwork 15, such as the Internet, to a server system 16 which periodically receives and stores the telemetered signals in a database 17, as further described below with reference to FIG. 2.

An example of a programmer 14 suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device to the internetwork 15, as is known in the art.

Other alternate telemetered signals transfer means could also be employed. For instance, the stored telemetered signals could be retrieved from the implantable medical device 12 and electronically transferred to the internetwork 15 using the combination of a remote external programmer and analyzer and a remote telephonic communicator, such as described in U.S. Pat. No. 5,113,869, the disclosure of which is incorporated herein by reference. Similarly, the stored telemetered signals could be retrieved and remotely downloaded to the server system 16 using a world-wide patient location and data telemetry system, such as described in U.S. Pat. No. 5,752,976, the disclosure of which is incorporated herein by reference.

The received telemetered signals are analyzed by the server system 16, which generates a patient status indicator. The feedback is then provided back to the patient 11 through a variety of means. By way of example, the feedback can be sent as an electronic mail message generated automatically by the server system 16 for transmission over the internetwork 15. The electronic mail message is received by a remote client 18, such as a personal computer (PC), situated for local access by the patient 11. Alternatively, the feedback can be sent through a telephone interface device 19 as an automated voice mail message to a telephone 21 or as an automated facsimile message to a facsimile machine 22, both also situated for local access by the patient 11. In addition to a remote client 18, telephone 21, and facsimile machine 22, feedback could be sent to other related devices, including a network computer, wireless computer, personal data assistant, television, or digital data processor. Preferably, the feedback is provided in a tiered fashion, as further described below with reference to FIG. 3.

Figure 2:
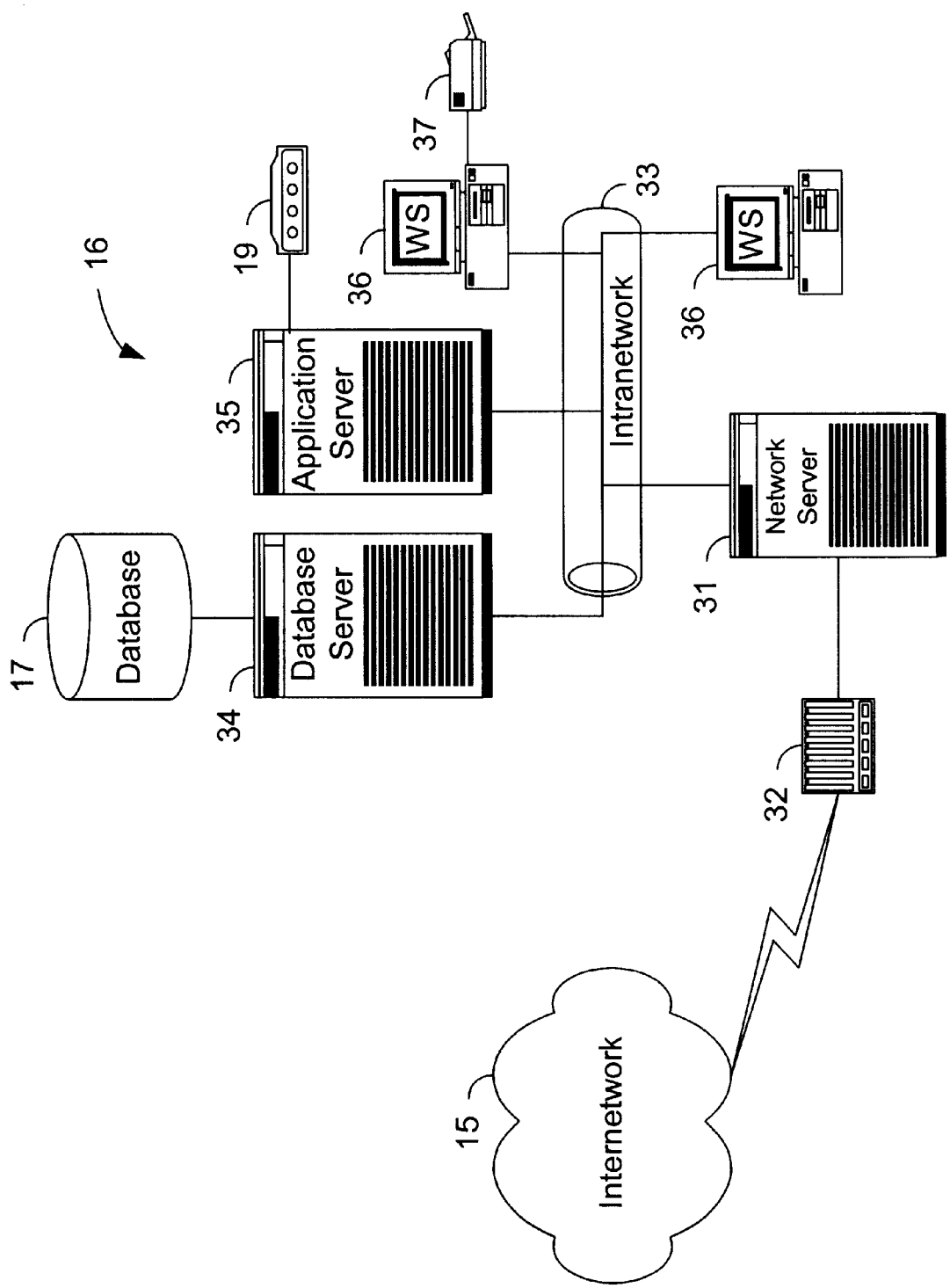
FIG. 2 is a block diagram showing the hardware components of the server system of the system of FIG. 1.

FIG. 2 is a block diagram showing the hardware components of the server system 16 of the system 10 of FIG. 1. The server system 16 consists of three individual servers: network server 31, database server 34, and application server 35. These servers are interconnected via an intranetwork 33. In the described embodiment, the functionality of the server system 16 is distributed among these three servers for efficiency and processing speed, although the functionality could also be performed by a single server or cluster of servers. The network server 31 is the primary interface of the server system 16 onto the internetwork 15. The network server 31 periodically receives the collected telemetered signals sent by remote implantable medical devices over the internetwork 15. The network server 31 is interfaced to the internetwork 15 through a router 32. To ensure reliable data exchange, the network server 31 implements a TCP/IP protocol stack, although other forms of network protocol stacks are suitable.

The database server 34 organizes the patient care records in the database 17 and provides storage of and access to information held in those records. A high volume of data in the form of collected measures sets from individual patients is received. The database server 34 frees the network server 31 from having to categorize and store the individual collected measures sets in the appropriate patient care record.

The application server 35 operates management applications and performs data analysis of the patient care records, as further described below with reference to FIG. 3. The application server 35 communicates feedback to the individual patients either through electronic mail sent back over the internetwork 15 via the network server 31 or as automated voice mail or facsimile messages through the telephone interface device 19.

The server system 16 also includes a plurality of individual workstations 36 (WS) interconnected to the intranetwork 33, some of which can include peripheral devices, such as a printer 37. The workstations 36 are for use by the data management and programming staff, nursing staff, office staff, and other consultants and authorized personnel.

The database 17 consists of a high-capacity storage medium configured to store individual patient care records and related health care information. Preferably, the database 17 is configured as a set of high-speed, high capacity hard drives, such as organized into a Redundant Array of Inexpensive Disks (RAID) volume. However, any form of volatile storage, non-volatile storage, removable storage, fixed storage, random access storage, sequential access storage, permanent storage, erasable storage, and the like would be equally suitable. The organization of the database 17 is further described below with reference to FIG. 3.

The individual servers and workstations are general purpose, programmed digital computing devices consisting of a central processing unit (CPU), random access memory (RAM, non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output transmittal, or storage. In the described embodiment, the individual servers are Intel Pentium-based server systems, such as available from Dell Computers, Austin, Tex., or Compaq Computers, Houston, Tex. Each system is preferably equipped with 128 MB RAM, 100 GB hard drive capacity, data backup facilities, and related hardware for interconnection to the intranetwork 33 and internetwork 15. In addition, the workstations 36 are also Intel Pentium-based personal computer or workstation systems, also available from Dell Computers, Austin, Tex., or Compaq Computers, Houston, Tex. Each workstation is preferably equipped with 64 MB RAM, 10 GB hard drive capacity, and related hardware for interconnection to the intranetwork 33. Other types of server and workstation systems, including personal computers, minicomputers, mainframe computers, supercomputers, parallel computers, workstations, digital data processors and the like would be equally suitable, as is known in the art.

The telemetered signals are communicated over an internetwork 15, such as the Internet. However, any type of electronic communications link could be used, including an intranetwork link, serial link, data telephone link, satellite link, radio-frequency link, infrared link, fiber optic link, coaxial cable link, television link, and the like, as is known in the art. Also, the network server 31 is interfaced to the internetwork 15 using a T-1 network router 32, such as manufactured by Cisco Systems, Inc., San Jose, Calif. However, any type of interfacing device suitable for interconnecting a server to a network could be used, including a data modem, cable modem, network interface, serial connection, data port, hub, frame relay, digital PBX, and the like, as is known in the art.

Figure 3:
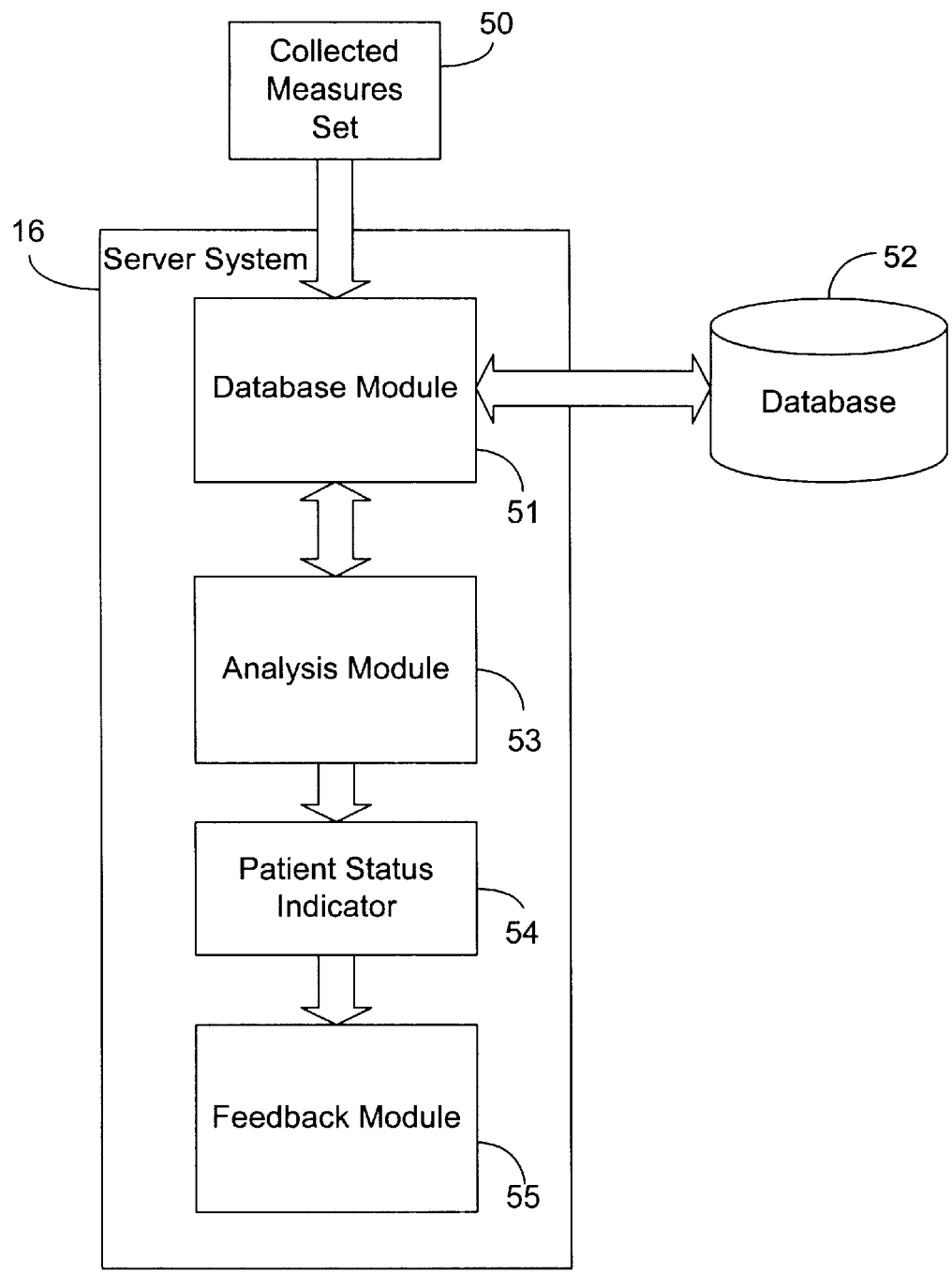
FIG. 3 is a block diagram showing the software modules of the server system of the system of FIG. 1.

FIG. 3 is a block diagram showing the software modules of the server system 16 of the system 10 of FIG. 1. Each module is a computer program written as source code in a conventional programming language, such as the C or Java programming languages, and is presented for execution by the CPU as object or byte code, as is known in the arts. The various implementations of the source code and object and byte codes can be held on a computer-readable storage medium or embodied on a transmission medium in a carrier wave. There are three basic software modules, which functionally define the primary operations performed by the server system 16: database module 51, analysis module 53, and feedback module 55. In the described embodiment, these modules are executed in a distributed computing environment, although a single server or a cluster of servers could also perform the functionality of the modules. The module functions are further described below in more detail beginning with reference to FIG. 7.

For each patient being provided remote patient care, the server system 16 periodically receives a collected measures set 50 which is forwarded to the database module 51 for processing. The database module 51 organizes the individual patent care records stored in the database 52 and provides the facilities for efficiently storing and accessing the collected measures sets 50 and patient data maintained in those records. An exemplary database schema for use in storing collected measures sets 50 in a patient care record is described below, by way of example, with reference to FIG. 5. The database server 34 (shown in FIG. 2) performs the functionality of the database module 51. Any type of database organization could be utilized, including a flat file system, hierarchical database, relational database, or distributed database, such as provided by database vendors, such as Oracle Corporation, Redwood Shores, Calif.

The analysis module 53 analyzes the collected measures sets 50 stored in the patient care records in the database 52. The analysis module 53 makes an automated determination of patient wellness in the form of a patient status indicator 54. Collected measures sets 50 are periodically received from implantable medical devices and maintained by the database module 51 in the database 52. Through the use of this collected information, the analysis module 53 can continuously follow the medical well being of a patient and can recognize any trends in the collected information that might warrant medical intervention. The analysis module 53 compares individual measures and derived measures obtained from both the care records for the individual patient and the care records for a disease specific group of patients or the patient population in general. The analytic operations performed by the analysis module 53 are further described below with reference to FIG. 4. The application server 35 (shown in FIG. 2) performs the functionality of the analysis module 53.

The feedback module 55 provides automated feedback to the individual patient based, in part, on the patient status indicator 54. As described above, the feedback could be by electronic mail or by automated voice mail or facsimile. Preferably, the feedback is provided in a tiered manner. In the described embodiment, four levels of automated feedback are provided. At a first level, an interpretation of the patient status indicator 54 is provided. At a second level, a notification of potential medical concern based on the patient status indicator 54 is provided. This feedback level could also be coupled with human contact by specially trained technicians or medical personnel. At a third level, the notification of potential medical concern is forwarded to medical practitioners located in the patient's geographic area. Finally, at a fourth level, a set of reprogramming instructions based on the patient status indicator 54 could be transmitted directly to the implantable medical device to modify the programming instructions contained therein. As is customary in the medical arts, the basic tiered feedback scheme would be modified in the event of bona fide medical emergency. The application server 35 (shown in FIG. 2) performs the functionality of the feedback module 55.

Figure 4:
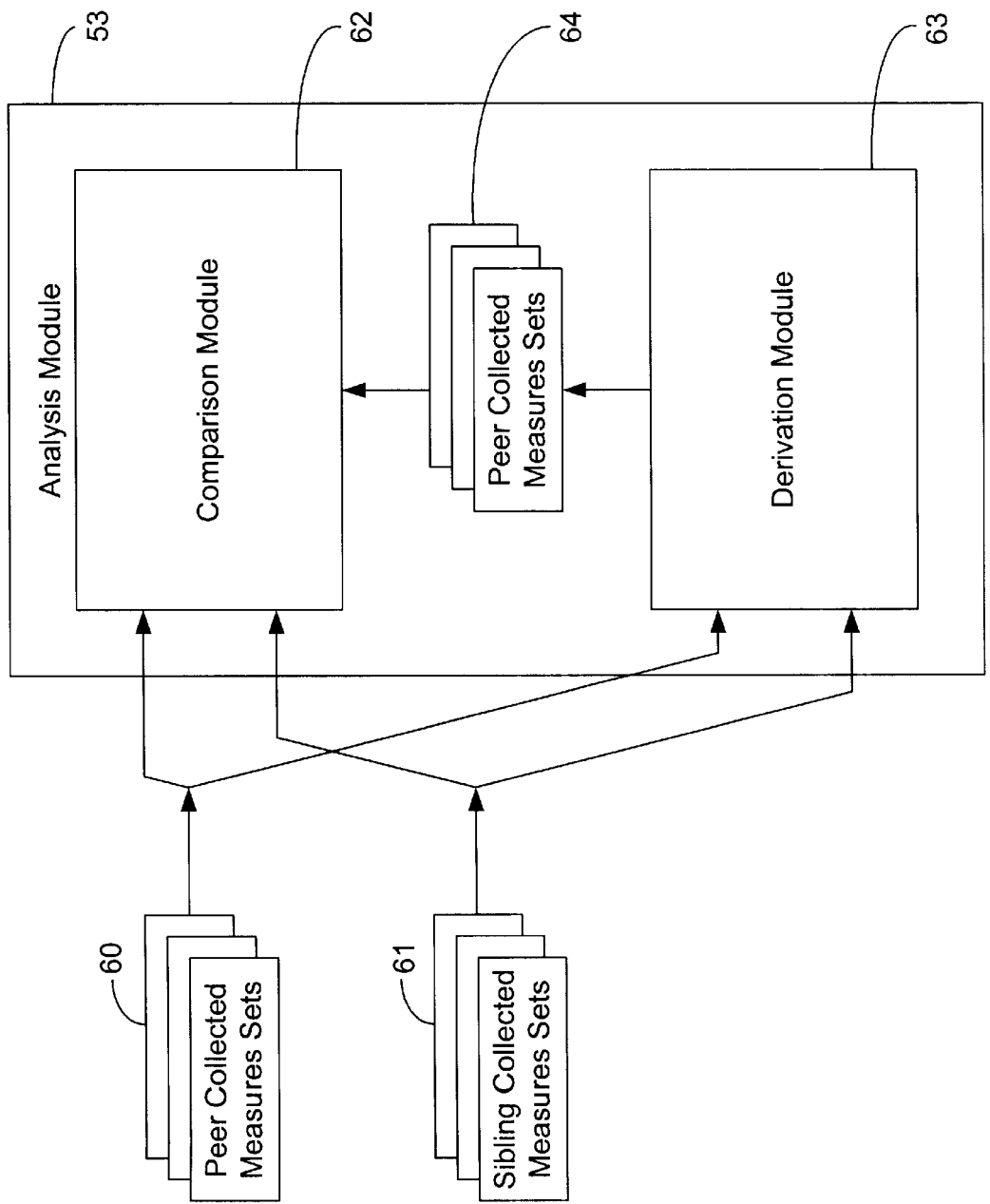
FIG. 4 is a block diagram showing the analysis module of the server system of FIG. 3.

FIG. 4 is a block diagram showing the analysis module 53 of the server system 16 of FIG. 3. The analysis module 53 contains two functional submodules: comparison module 62 and derivation module 63. The purpose of the comparison module 62 is to compare two or more individual measures, either collected or derived. The purpose of the derivation module 63 is to determine a derived measure based on one or more collected measures which is then used by the comparison module 62. For instance, a new and improved indicator of impending heart failure could be derived based on the exemplary cardiac collected measures set described with reference to FIG. 5. The analysis module 53 can operate either in a batch mode of operation wherein patient status indicators are generated for a set of individual patients or in a dynamic mode wherein a patient status indicator is generated on the fly for an individual patient.

The comparison module 62 receives as inputs from the database 17 two input sets functionally defined as peer collected measures sets 60 and sibling collected measures sets 61, although in practice, the collected measures sets are stored on a per sampling basis. Peer collected measures sets 60 contain individual collected measures sets that all relate to the same type of patient information, for instance, atrial electrical activity, but which have been periodically collected over time. Sibling collected measures sets 61 contain individual collected measures sets that relate to different types of patient information, but which may have been collected at the same time or different times. In practice, the collected measures sets are not separately stored as "peer" and "sibling" measures. Rather, each individual patient care record stores multiple sets of sibling collected measures. The distinction between peer collected measures sets 60 and sibling collected measures sets 61 is further described below with reference to FIG. 6.

The derivation module 63 determines derived measures sets 64 on an as-needed basis in response to requests from the comparison module 62. The derived measures 64 are determined by performing linear and non-linear mathematical operations on selected peer measures 60 and sibling measures 61, as is known in the art.

FIG. 5 is a database schema showing, by way of example, the organization of a cardiac patient care record stored 70 in the database 17 of the system 10 of FIG. 1. Only the information pertaining to collected measures sets are shown. Each patient care record would also contain normal identifying and treatment profile information, as well as medical history and other pertinent data (not shown). Each patient care record stores a multitude of collected measures sets for an individual patient. Each individual set represents a recorded snapshot of telemetered signals data which was recorded, for instance, per heartbeat or binned average basis by the implantable medical device 12. For example, for a cardiac patient, the following information would be recorded as a collected measures set: atrial electrical activity 71, ventricular electrical activity 72, time of day 73, activity level 74, cardiac output 75, oxygen level 76, cardiovascular pressure measures 77, pulmonary measures 78, interventions made by the implantable medical device 78, and the relative success of any interventions made 80. In addition, the implantable medical device 12 would also communicate device specific information, including battery status 81 and program settings 82. Other types of collected measures are possible. In addition, a well-documented set of derived measures can be determined based on the collected measures, as is known in the art.

FIG. 6 is a record view showing, by way of example, a set of partial cardiac patient care records stored in the database 17 of the system 10 of FIG. 1. Three patient care records are shown for Patient 1, Patient 2, and Patient 3. For each patent, three sets of measures are shown, X, Y, and Z. The measures are organized into sets with Set 0 representing sibling measures made at a reference time t=0. Similarly, Set n−2, Set n−1 and Set n each represent sibling measures made at later reference times t=n−2, t=n−1 and t=n, respectively.

For a given patient, for instance, Patient 1, all measures representing the same type of patient information, such as measure X, are peer measures. These are measures, which are monitored over time in a disease-matched peer group. All measures representing different types of patient information, such as measures X, Y, and Z, are sibling measures. These are measures which are also measured over time, but which might have medically significant meaning when compared to each other within a single set. Each of the measures, X, Y, and Z, could be either collected or derived measures.

The analysis module 53 (shown in FIG. 4) performs two basic forms of comparison. First, individual measures for a given patient can be compared to other individual measures for that same patient These comparisons might be peer-to-peer measures projected over time, for instance, $X_n$, $X_{n-1}$, $X_{n-2}$, ... $X_0$, or sibling-to-sibling measures for a single snapshot, for instance, $X_n$, $Y_n$, and $Z_n$, or projected over time, for instance, $X_n$, $Y_n$, $Z_n$, $X_{n-1}$, $Y_{n-1}$, $Z_{n-1}$, $X_{n-2}$, $Y_{n-2}$, $Z_{n-2}$, ... $X_0$, $Y_0$, $Z_0$. Second, individual measures for a given patient can be compared to other individual measures for a group of other patients sharing the same disease-specific characteristics or to the patient population in general. Again, these comparisons might be peer-to-peer measures projected over time, for instance, $X_n$, $X_{n'}$, $X_{n''}$, $X_{n-1}$, $X_{n-1'}$, $X_{n-1''}$, $X_{n-2}$, $X_{n-2'}$, $X_{n-2''}$ ... $X_0$, $X_{0'}$, $X_{0''}$, or comparing the individual patient's measures to an average from the group. Similarly, these comparisons might be sibling-to-sibling measures for single snapshots, for instance, $X_n$, $X_{n'}$, $X_{n''}$, $Y_n$, $Y_{n'}$, $Y_{n''}$, and $Z_n$, $Z_{n'}$, $Z_{n''}$, or projected over time, for instance, $X_n$, $X_{n'}$, $X_{n''}$, $Y_n$, $Y_{n'}$, $Y_{n''}$, $Z_n$, $Z_{n'}$, $Z_{n''}$, $X_{n-1}$, $X_{n-1'}$, $X_{n-1''}$, $Y_{n-1}$, $Y_{n-1'}$, $Y_{n-1''}$, $Z_{n-1}$, $Z_{n-1'}$, $Z_{n-1''}$, $X_{n-2}$, $X_{n-2'}$, $x_{n-2''}$, $Y_{n-2}$, $Y_{n-2'}$, $Y_{n-2''}$, $Z_{n-2}$, $Z_{n-2'}$, $z_{n-2''}$ ... $X_0$, $X_{0'}$, $X_{0''}$, $Y_0$, $Y_{0'}$, $Y_{0''}$, and $Z_0$, $Z_{0'}$, $Z_{0''}$. Other forms of comparisons are feasible.

Figure 7:
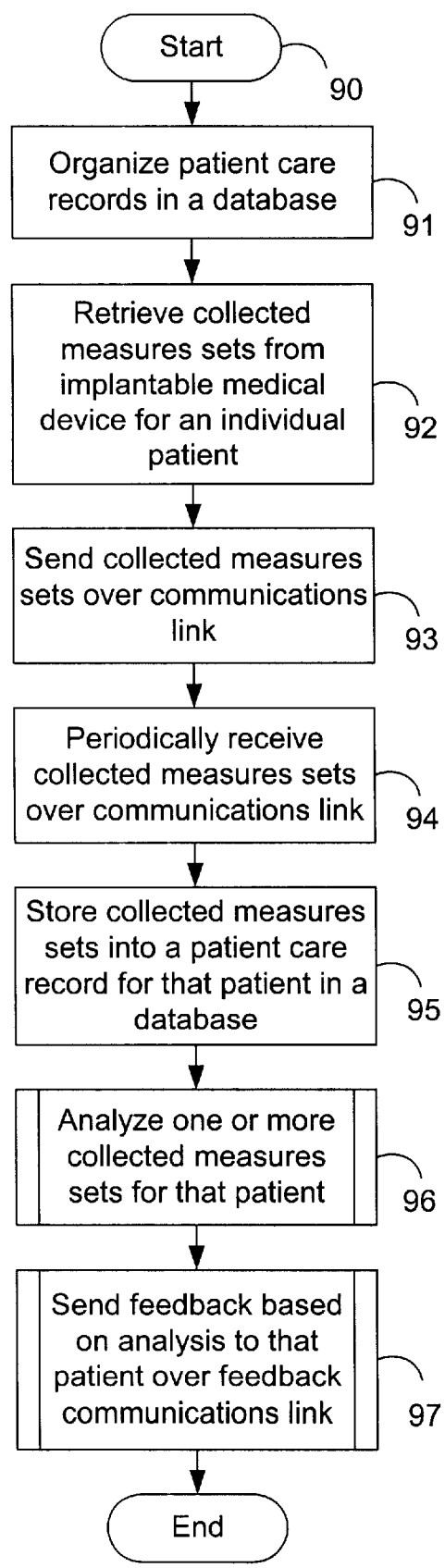
FIG. 7 is a flow diagram showing a method for automated collection and analysis of patient information retrieved from an implantable medical device for remote patient care in accordance with the present invention.

FIG. 7 is a flow diagram showing a method 90 for automated collection and analysis of patient information retrieved from an implantable medical device 12 for remote patient care in accordance with the present invention. The method 90 is implemented as a conventional computer program for execution by the server system 16 (shown in FIG. 1). As a preparatory step, the patient care records are organized in the database 17 with a unique patient care record assigned to each individual patient (block 91). Next, the collected measures sets for an individual patient are retrieved from the implantable medical device 12 (block 92) using a programmer, interrogator, telemetered signals transceiver, and the like. The retrieved collected measures sets are sent, on a substantially regular basis, over the internetwork 15 or similar communications link (block 93) and periodically received by the server system 16 (block 94). The collected measures sets are stored into the patient care record in the database 17 for that individual patient (block 95). One or more of the collected measures sets for that patient are analyzed (block 96), as further described below with reference to FIG. 8. Finally, feedback based on the analysis is sent to that patient over the internetwork 15 as an email message, via telephone line as an automated voice mail or facsimile message, or by similar feedback communications link (block 97), as further described below with reference to FIG. 11.

Figure 8:
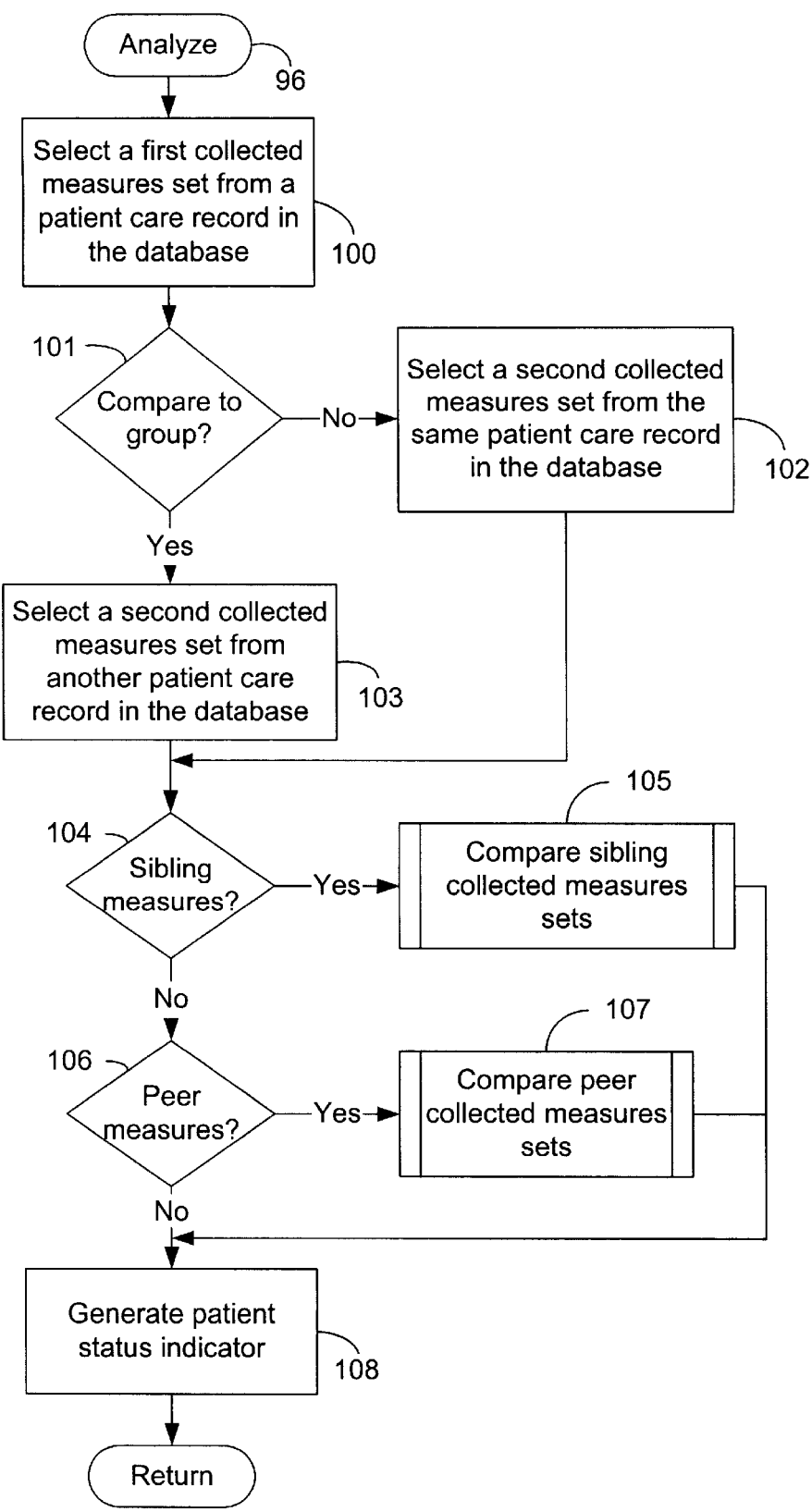
FIG. 8 is a flow diagram showing a routine for analyzing collected measures sets for use in the method of FIG. 7.

FIG. 8 is a flow diagram showing the routine for analyzing collected measures sets 96 for use in the method of FIG.

7. The purpose of this routine is to make a determination of general patient wellness based on comparisons and heuristic trends analyses of the measures, both collected and derived, in the patient care records in the database 17. A first collected measures set is selected from a patient care record in the database 17 (block 100). If the measures comparison is to be made to other measures originating from the patient care record for the same individual patient (block 101), a second collected measures set is selected from that patient care record (block 102). Otherwise, a group measures comparison is being made (block 101) and a second collected measures set is selected from another patient care record in the database 17 (block 103). Note the second collected measures set could also contain averaged measures for a group of disease specific patients or for the patient population in general.

Next, if a sibling measures comparison is to be made (block 104), a routine for comparing sibling collected measures sets is performed (block 105), as further described below with reference to FIG. 9. Similarly, if a peer measures comparison is to be made (block 106), a routine for comparing sibling collected measures sets is performed (block 107), as further described below with reference to FIGS. 10A and 10B.

Finally, a patient status indicator is generated (block 108). By way of example, cardiac output could ordinarily be approximately 5.0 liters per minute with a standard deviation of ±1.0. An actionable medical phenomenon could occur when the cardiac output of a patient is ±3.0–4.0 standard deviations out of the norm. A comparison of the cardiac output measures 75 (shown in FIG. 5) for an individual patient against previous cardiac output measures 75 would establish the presence of any type of downward health trend as to the particular patient. A comparison of the cardiac output measures 75 of the particular patient to the cardiac output measures 75 of a group of patients would establish whether the patient is trending out of the norm. From this type of analysis, the analysis module 53 generates a patient status indicator 54 and other metrics of patient wellness, as is known in the art.

Figure 9:
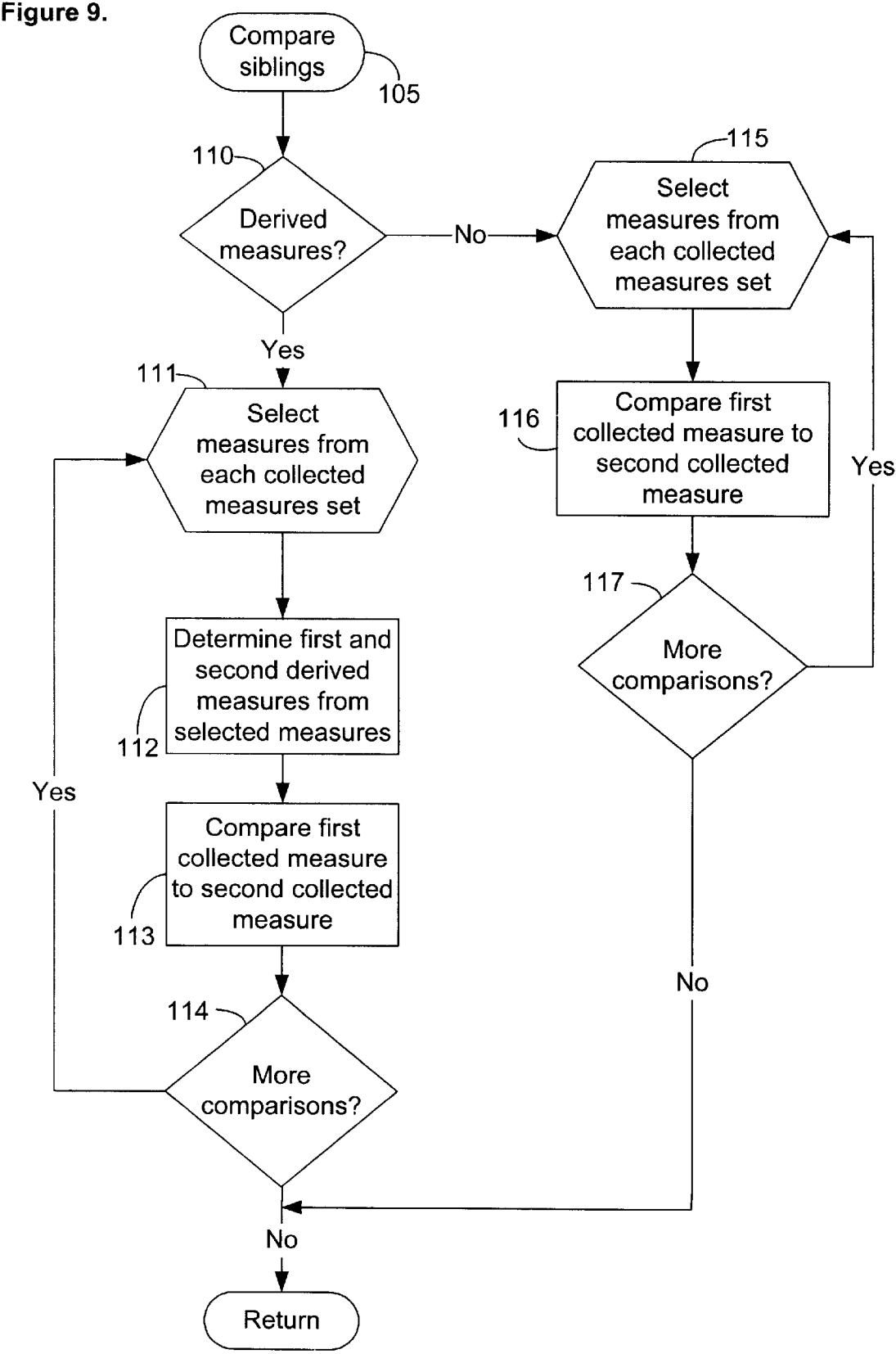
FIG. 9 is a flow diagram showing a routine for comparing sibling collected measures sets for use in the routine of FIG. 8.

FIG. 9 is a flow diagram showing the routine for comparing sibling collected measures sets 105 for use in the routine of FIG. 8. Sibling measures originate from the patient care records for an individual patient. The purpose of this routine is either to compare sibling derived measures to sibling derived measures (blocks 111–113) or sibling collected measures to sibling collected measures (blocks 115–117). Thus, if derived measures are being compared (block 110), measures are selected from each collected measures set (block 111). First and second derived measures are derived from the selected measures (block 112) using the derivation module 63 (shown in FIG. 4). The first and second derived measures are then compared (block 113) using the comparison module 62 (also shown in FIG. 4). The steps of selecting, determining, and comparing (blocks 111–113) are repeated until no further comparisons are required (block 114), whereupon the routine returns.

If collected measures are being compared (block 110), measures are selected from each collected measures set (block 115). The first and second collected measures are then compared (block 116) using the comparison module 62 (also shown in FIG. 4). The steps of selecting and comparing (blocks 115–116) are repeated until no further comparisons are required (block 117), whereupon the routine returns.

Figure 10A:
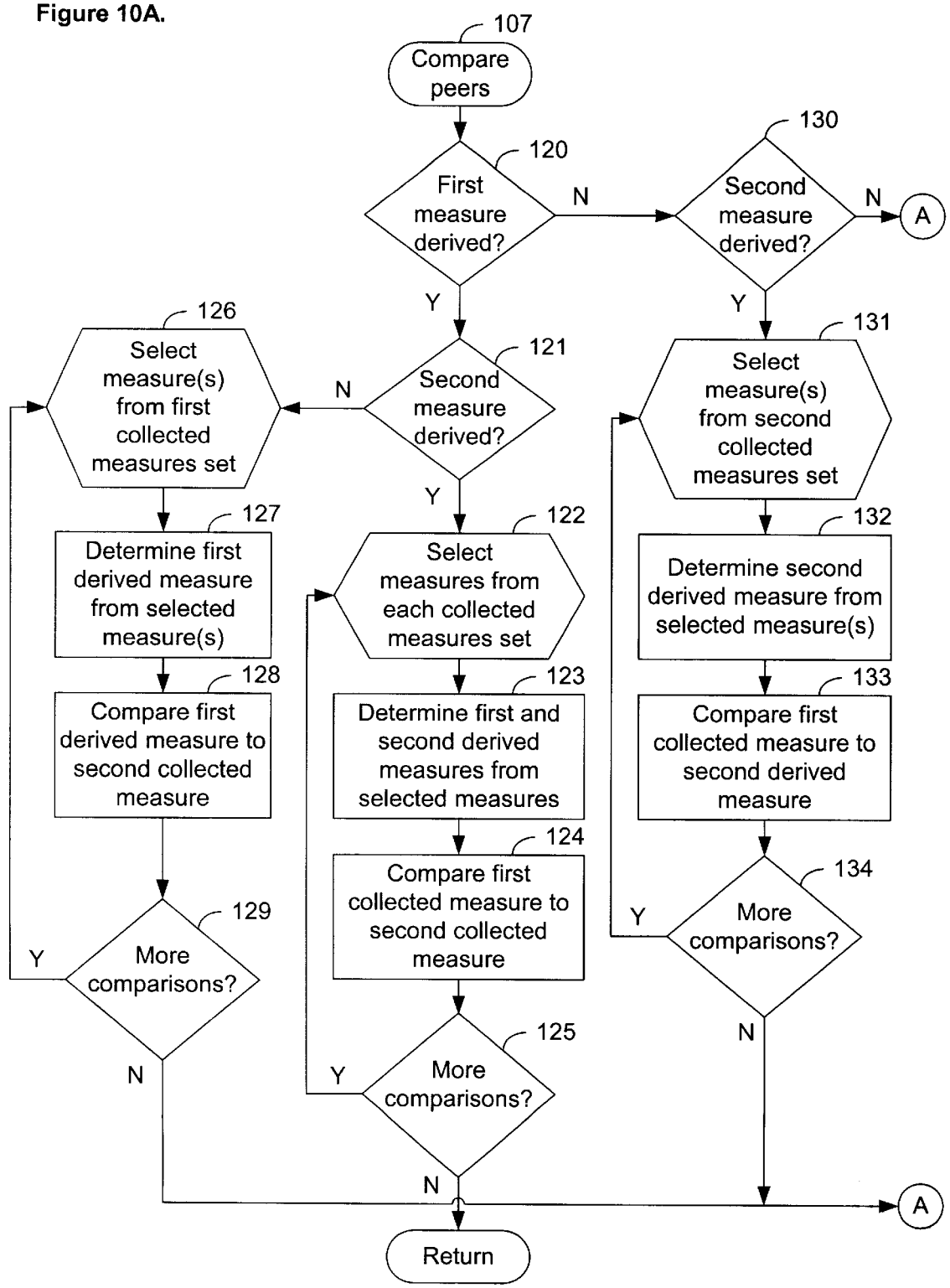
FIGS. 10A and 10B are flow diagrams showing a routine for comparing peer collected measures sets for use in the routine of FIG. 8.
Figure 10B:
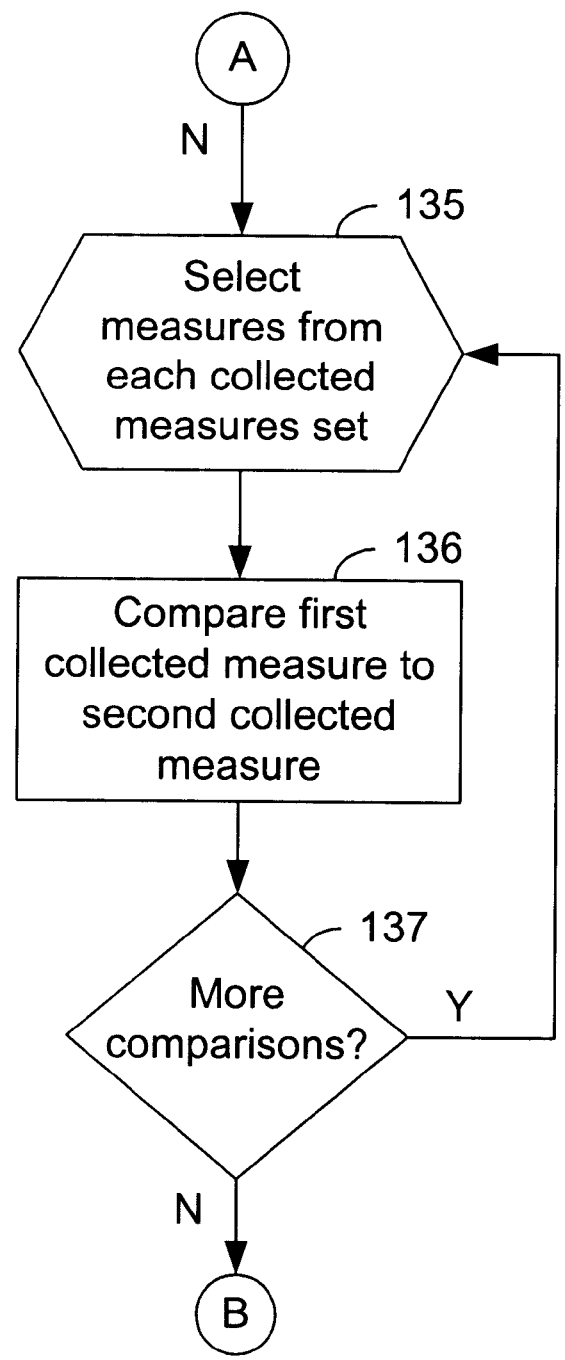

FIGS. 10A and 10B are a flow diagram showing the routine for comparing peer collected measures sets 107 for use in the routine of FIG. 8. Peer measures originate from patient care records for different patients, including groups of disease specific patients or the patient population in general. The purpose of this routine is to compare peer derived measures to peer derived measures (blocks 122–125), peer derived measures to peer collected measures (blocks 126–129), peer collected measures to peer derived measures (block 131–134), or peer collected measures to peer collected measures (blocks 135–137). Thus, if the first measure being compared is a derived measure (block 120) and the second measure being compared is also a derived measure (block 121), measures are selected from each collected measures set (block 122). First and second derived measures are derived from the selected measures (block 123) using the derivation module 63 (shown in FIG. 4). The first and second derived measures are then compared (block 124) using the comparison module 62 (also shown in FIG. 4). The steps of selecting, determining, and comparing (blocks 122–124) are repeated until no further comparisons are required (block 115), whereupon the routine returns.

If the first measure being compared is a derived measure (block 120) but the second measure being compared is a collected measure (block 121), a first measure is selected from the first collected measures set (block 126). A first derived measure is derived from the first selected measure (block 127) using the derivation module 63 (shown in FIG. 4). The first derived and second collected measures are then compared (block 128) using the comparison module 62 (also shown in FIG. 4). The steps of selecting, determining, and comparing (blocks 126–128) are repeated until no further comparisons are required (block 129), whereupon the routine returns.

If the first measure being compared is a collected measure (block 120) but the second measure being compared is a derived measure (block 130), a second measure is selected from the second collected measures set (block 131). A second derived measure is derived from the second selected measure (block 132) using the derivation module 63 (shown in FIG. 4). The first collected and second derived measures are then compared (block 133) using the comparison module 62 (also shown in FIG. 4). The steps of selecting, determining, and comparing (blocks 131–133) are repeated until no further comparisons are required (block 134), whereupon the routine returns.

If the first measure being compared is a collected measure (block 120) and the second measure being compared is also a collected measure (block 130), measures are selected from each collected measures set (block 135). The first and second collected measures are then compared (block 136) using the comparison module 62 (also shown in FIG. 4). The steps of selecting and comparing (blocks 135–136) are repeated until no further comparisons are required (block 137), whereupon the routine returns.

Figure 11:
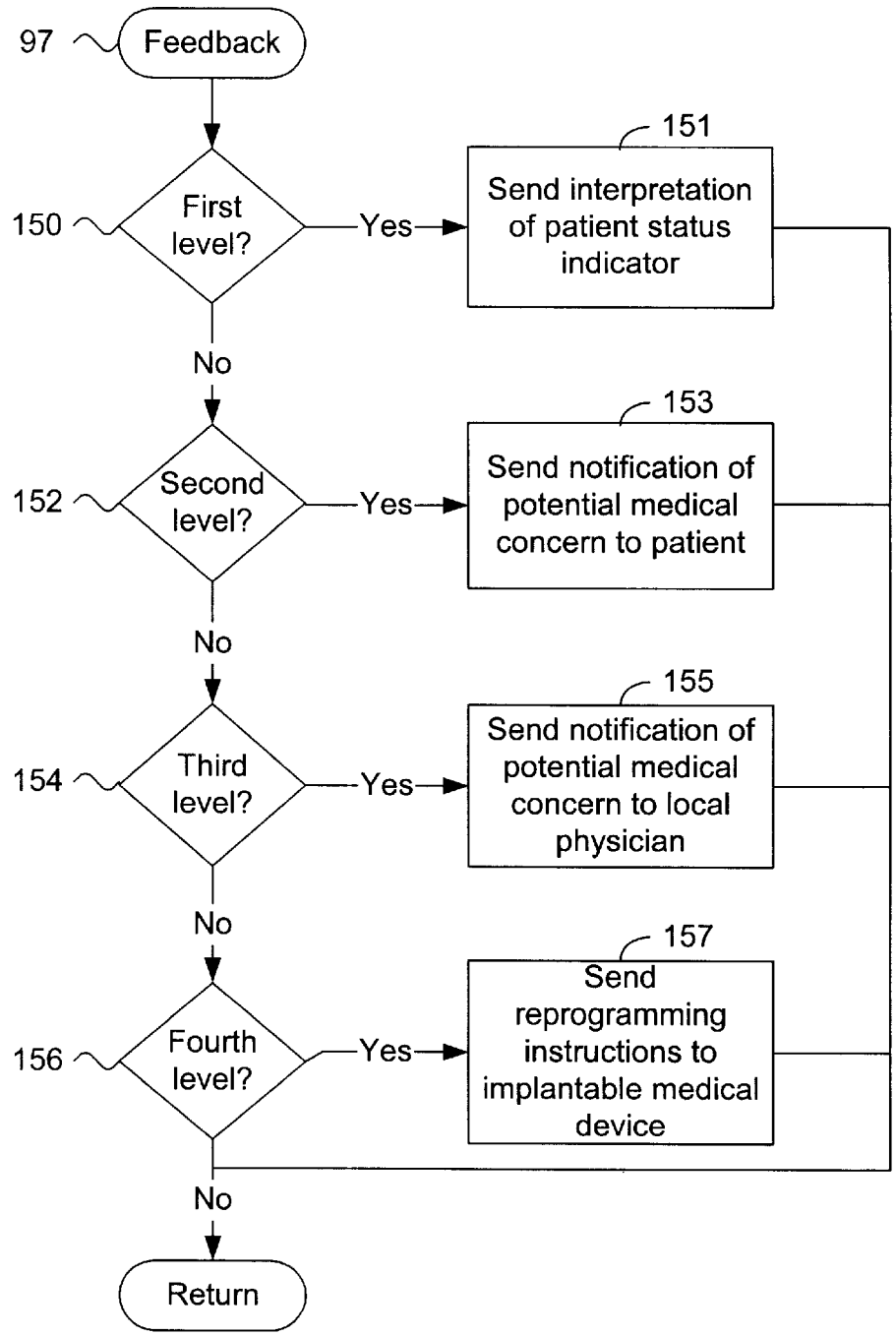
FIG. 11 is a flow diagram showing a routine for providing feedback for use in the method of FIG. 7.

FIG. 11 is a flow diagram showing the routine for providing feedback 97 for use in the method of FIG. 7. The purpose of this routine is to provide tiered feedback based on the patient status indicator. Four levels of feedback are provided with increasing levels of patient involvement and medical care intervention. At a first level (block 150), an interpretation of the patient status indicator 54, preferably phrased in lay terminology, and related health care information is sent to the individual patient (block 151) using the feedback module 55 (shown in FIG. 3). At a second level (block 152), a notification of potential medical concern, based on the analysis and heuristic trends analysis, is sent to the individual patient (block 153) using the feedback module 55. At a third level (block 154), the notification of potential medical concern is forwarded to the physician responsible for the individual patient or similar health care professionals (block 155) using the feedback module 55. Finally, at a fourth level (block 156), reprogramming instructions are sent to the implantable medical device 12 (block 157) using the feedback module 55.

Figure 12:
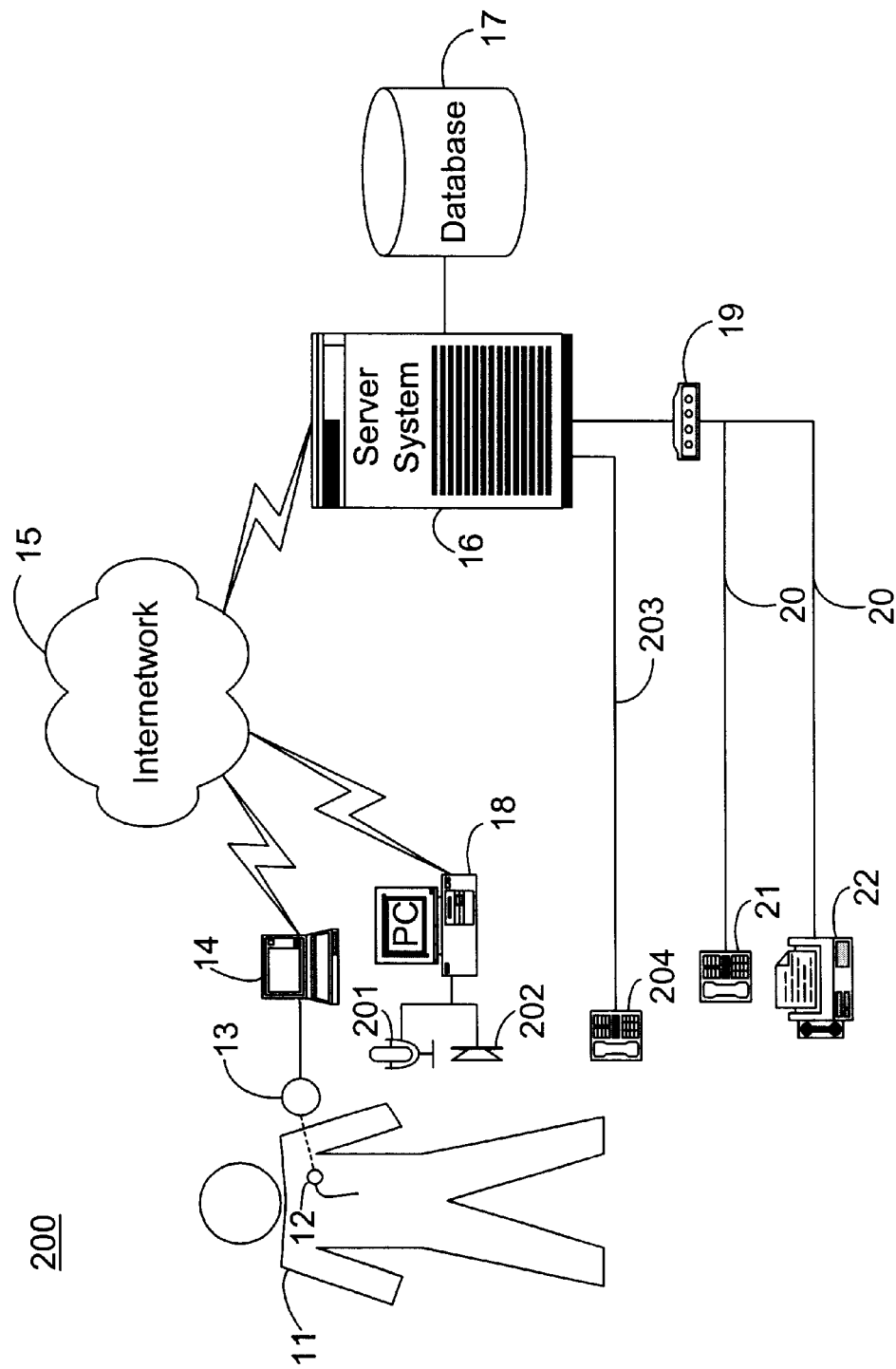
FIG. 12 is a block diagram showing a system for providing normalized voice feedback from an individual patient in an automated collection and analysis patient care system.

FIG. 12 is a block diagram showing a system 200 for providing normalized voice feedback from an individual patient 11 in an automated collection and analysis patient care system, such as the system 10 of FIG. 1. The remote client 18 includes a microphone 201 and a speaker 202 which is interfaced internally within the remote client 18 to sound recordation and reproduction hardware. The patient 11 provides spoken feedback into the microphone 201 in response to voice prompts reproduced by the remote client 18 on the speaker 202, as further described below with reference to FIG. 13. The raw spoken feedback is processed into a normalized set of quality of life measures which each relate to uniform self-assessment indicators, as further described below with reference to FIG. 15. Alternatively, in a further embodiment of the system 200, the patient 11 can provide spoken feedback via a telephone network 203 using a standard telephone 203, including a conventional wired telephone or a wireless telephone, such as a cellular telephone, as further described below with reference to FIG. 20. In the described embodiment, the microphone 201 and the speaker 202 are standard, off-the-shelf components commonly included with consumer personal computer systems, as is known in the art.

The system 200 continuously monitors and collects sets of device measures from the implantable medical device 12. To augment the on-going monitoring process with a patient's self-assessment of physical and emotional well-being, a quality of life measures set can be recorded by the remote client 18 Importantly, each quality of life measures set is recorded substantially contemporaneous to the collection of an identified collected device measures set. The date and time of day at which the quality of life measures set was recorded can be used to correlate the quality of life measures set to the collected device measures set recorded closest in time to the quality of life measures set. The pairing of the quality of life measures set and an identified collected device measures set provides medical practitioners with a more complete picture of the patient's medical status by combining physiological "hard" machine-recorded data with semi-quantitative "soft" patient-provided data.

Figure 13:
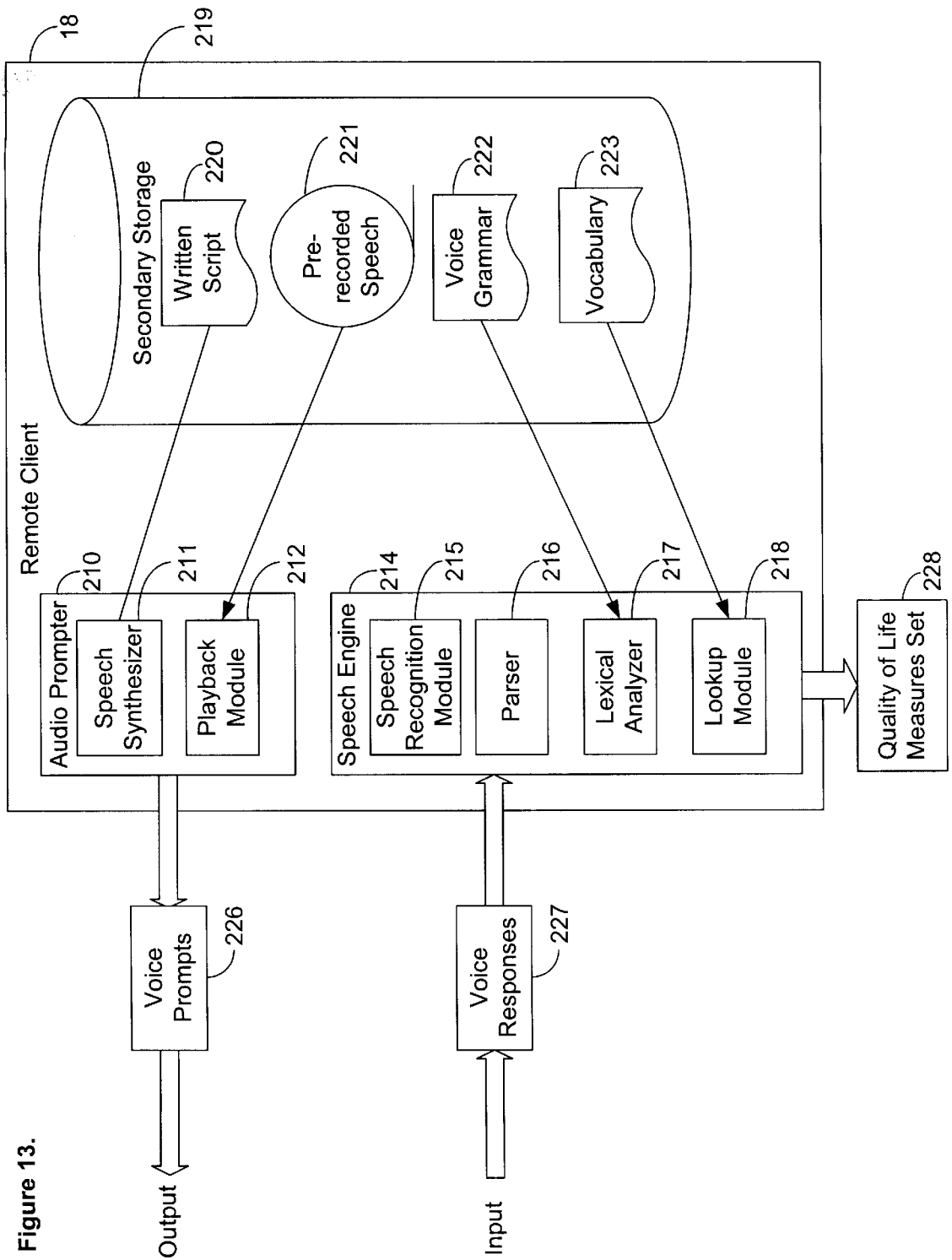
FIG. 13 is a block diagram showing the software modules of the remote client of the system of FIG. 12.

FIG. 13 is a block diagram showing the software modules of the remote client 18 of the system 200 of FIG. 12. As with the software modules of the system 10 of FIG. 1, each module here is also a computer program written as source code in a conventional programming language, such as the C or Java programming languages, and is presented for execution by the CPU as object or byte code, as is known in the arts. There are two basic software modules, which functionally define the primary operations performed by the remote client 18 in providing normalized voice feedback: audio prompter 210 and speech engine 214. The remote client 18 includes a secondary storage 219, such as a hard drive, a CD ROM player, and the like, within which is stored data used by the software modules. Conceptually, the voice reproduction and recognition functions performed by the audio prompter 210 and speech engine 214 can be described separately, but those same functions could also be performed by a single voice processing module, as is known in the art.

The audio prompter 210 generates voice prompts 226 which are played back to the patient 11 on the speaker 202. Each voice prompt is in the form of a question or phrase seeking to develop a self-assessment of the patient's physical and emotional well being. For example, the patient 11 might be prompted with, "Are you short of breath?" The voice prompts 226 are either from a written script 220 reproduced by speech synthesizer 211 or pre-recorded speech 221 played back by playback module 212. The written script 220 is stored within the secondary storage 219 and consists of written quality of life measure requests. Similarly, the pre-recorded speech 221 is also stored within the secondary storage 219 and consists of sound "bites" of recorded quality of life measure requests in either analog or digital format.

The speech engine 214 receives voice responses 227 spoken by the patient 11 into the microphone 201. The voice responses 227 can be unstructured, natural language phrases and sentences. A voice grammar 222 provides a lexical structuring for use in determining the meaning of each spoken voice response 227. The voice grammar 222 allows the speech engine 214 to "normalize" the voice responses 227 into recognized quality of life measures 228. Individual spoken words in each voice response 227 are recognized by a speech recognition module 215 and translated into written words. In turn, the written words are parsed into tokens by a parser 216. A lexical analyzer 217 analyzes the tokens as complete phrases in accordance with a voice grammar 222 stored within the secondary storage 219. Finally, if necessary, the individual words are normalized to uniform terms by a lookup module 218 which retrieves synonyms maintained as a vocabulary 223 stored within the secondary storage 218. For example, in response to the query, "Are you short of breath?," a patient might reply, "I can hardly breath," "I am panting," or "I am breathless." The speech recognition module 215 would interpret these phrases to imply dyspnea with a corresponding quality of life measure indicating an awareness by the patient of abnormal breathing. In the described embodiment, the voice reproduction and recognition functions can be performed by the various natural voice software programs licensed by Dragon Systems, Inc., Newton, Mass. Alternatively, the written script 220, voice grammar 222, and vocabulary 223 could be expressed as a script written in a voice page markup language for interpretation by a voice browser operating on the remote client 18. Two exemplary voice page description languages include the VoxML markup language, licensed by Motorola, Inc., Chicago, Ill., and described at http://www.voxml.com, and the Voice eXtensible Markup Language (VXML), currently being jointly developed by AT&T, Motorola, Lucent Technologies, and IBM, and described at http://www.vxmlforum.com. The module functions are further described below in more detail beginning with reference to FIGS. 16A–16B.

Figure 14:
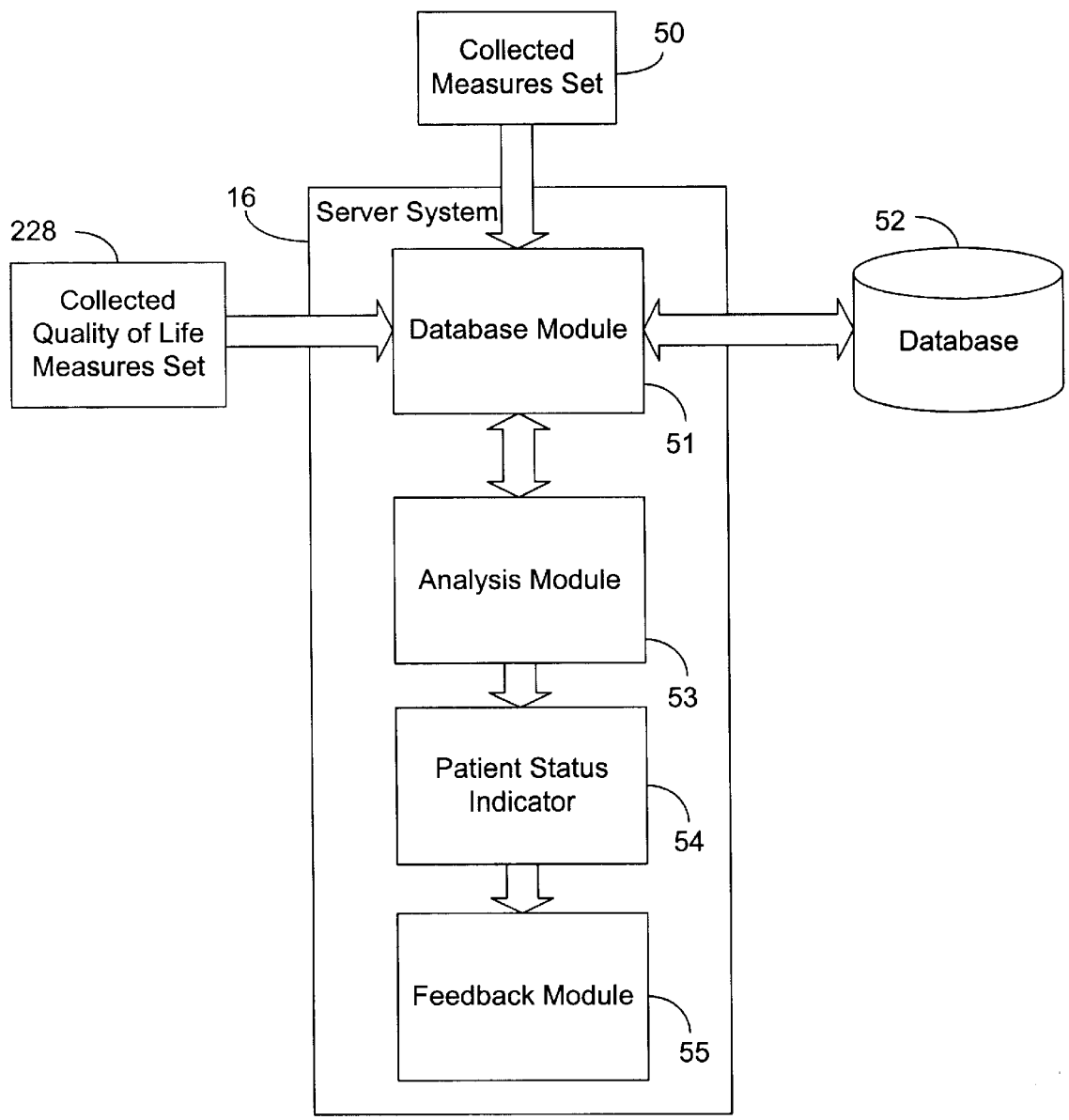
FIG. 14 is a block diagram showing the software modules of the server system of the system of FIG. 12.

FIG. 14 is a block diagram showing the software modules of the server system 16 of the system 200 of FIG. 12. The database module 51, previously described above with reference to FIG. 3, also receives the collected quality of life measures set 228 from the remote client 18, which the database module 51 stores into the appropriate patient care record in the database 52. The date and time of day 236 (shown in FIG. 15) of the quality of life measures set 228 is matched to the date and time of day 73 (shown in FIG. 5) of the collected measures set 50 recorded closest in time to the quality of life measures set 228. The matching collected measures set 50 is identified in the patient care record and can be analyzed with the quality of life measures set 228 by the analysis module 53, such as described above with reference to FIG. 8.

Figure 15:
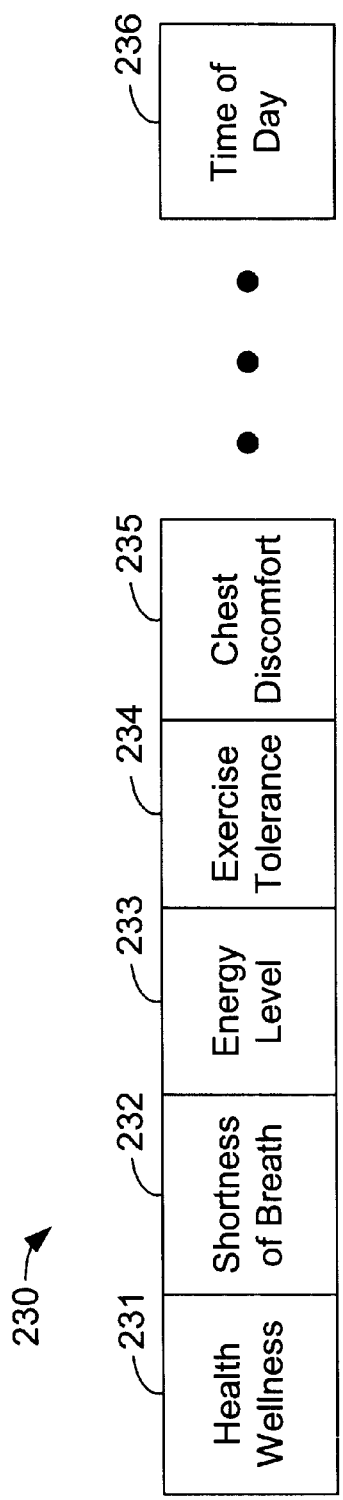
FIG. 15 is a database schema showing, by way of example, the organization of a quality of life record for cardiac patient care stored as part of a patient care record in the database of the system of FIG. 12.

FIG. 15 is a database schema showing, by way of example, the organization of a quality of life record 230 for cardiac patient care stored as part of a patient care record in the database 17 of the system 200 of FIG. 12. A quality of life score is a semi-quantitative self-assessment of an individual patient's physical and emotional well being. Non-commercial, non-proprietary standardized automated quality of life scoring systems are readily available, such as provided by the Duke Activities Status Indicator. For example, for a cardiac patient, the quality of life record 230 stores the following information: health wellness 231, shortness of breath 232, energy level 233, chest discomfort 235, time of day 234, and other quality of life measures as would be known to one skilled in the art. Other types of quality of life measures are possible.

A quality of life indicator is a vehicle through which a patient can remotely communicate to the patient care system how he or she is subjectively feeling. The quality of life indicators can include symptoms of disease. When tied to machine-recorded physiological measures, a quality of life indicator can provide valuable additional information to medical practitioners and the automated collection and analysis patient care system 200 not otherwise discernible without having the patient physically present. For instance, a scoring system using a scale of 1.0 to 10.0 could be used with 10.0 indicating normal wellness and 1.0 indicating severe health problems. Upon the completion of an initial observation period, a patient might indicate a health wellness score 231 of 5.0 and a cardiac output score of 5.0. After one month of remote patient care, the patient might then indicate a health wellness score 231 of 4.0 and a cardiac output score of 4.0 and a week later indicate a health wellness score 231 of 3.5 and a cardiac output score of 3.5. Based on a comparison of the health wellness scores 231 and the cardiac output scores, the system 200 would identify a trend indicating the necessity of potential medical intervention while a comparison of the cardiac output scores alone might not lead to the same prognosis.

Figure 16A:
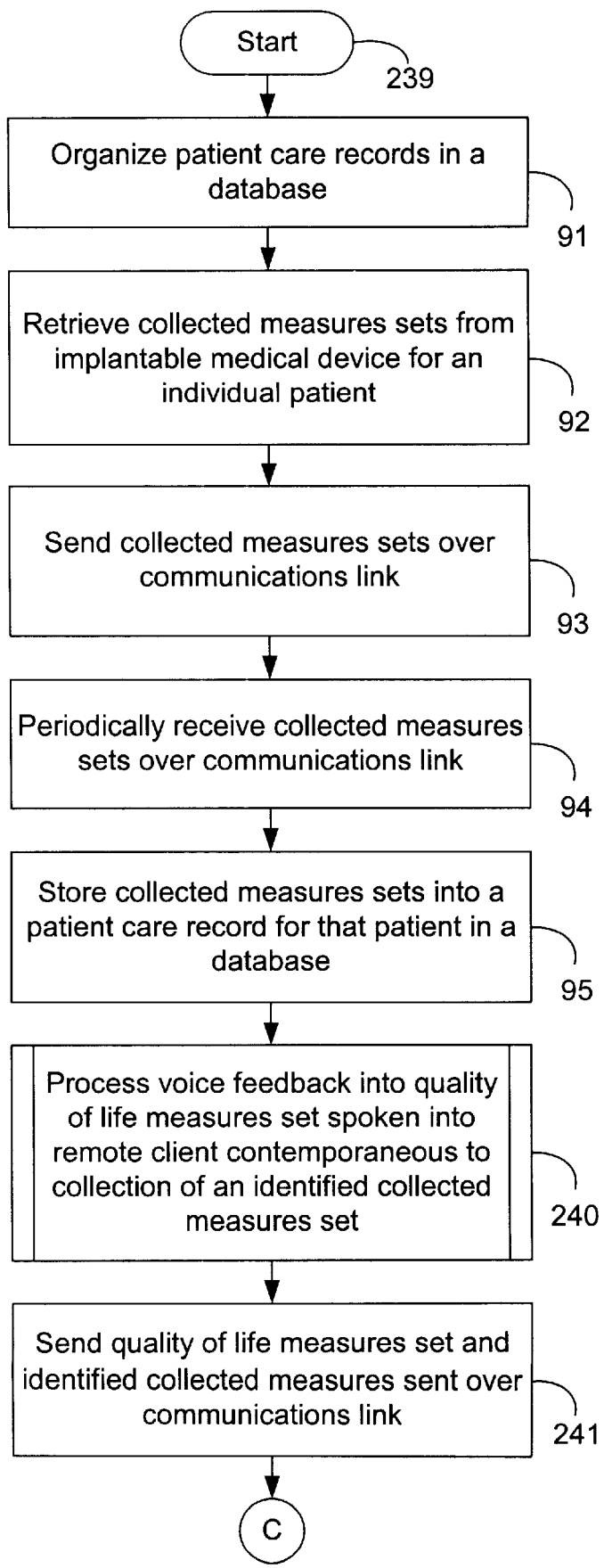
FIGS. 16A–16B are flow diagrams showing a method for providing normalized voice feedback from an individual patient in an automated collection and analysis patient care system.
Figure 16B:
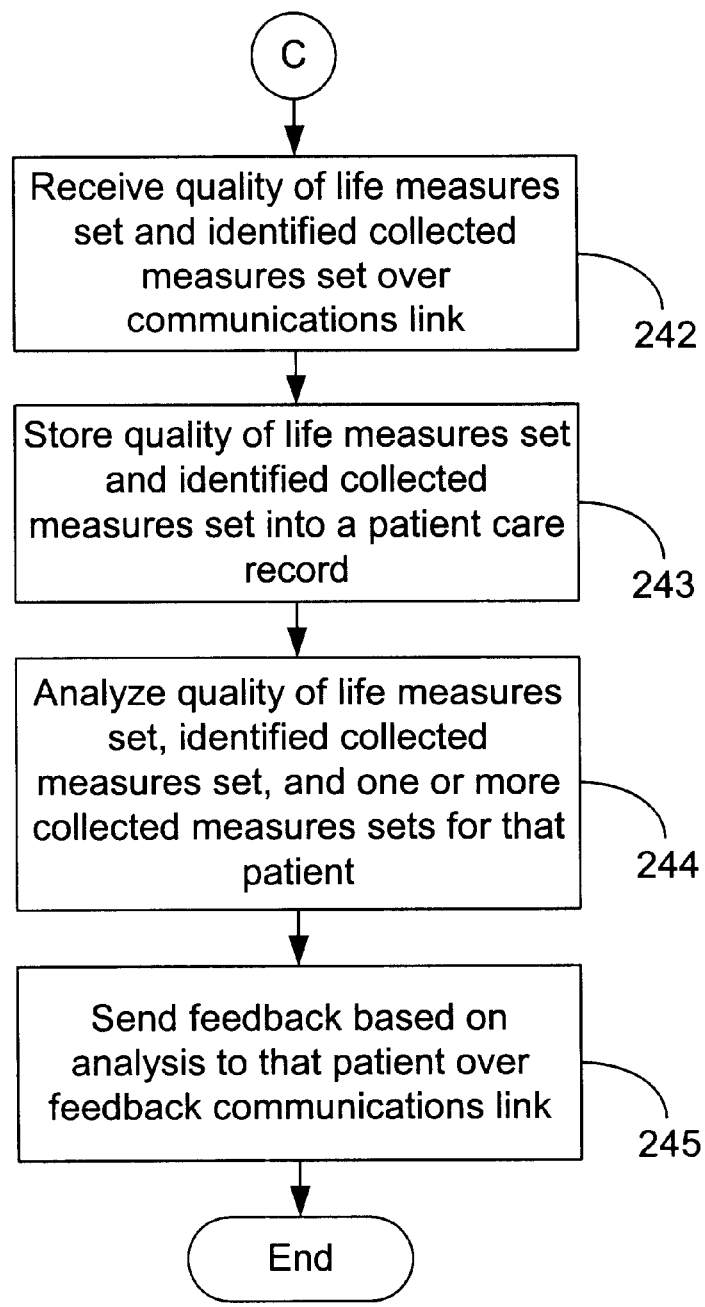

FIGS. 16A–16B are flow diagrams showing a method 239 for providing normalized voice feedback from an individual patient 11 in an automated collection and analysis patient care system 200. As with the method 90 of FIG. 7, this method is also implemented as a conventional computer program and performs the same set of steps as described with reference to FIG. 7 with the following additional functionality. First, voice feedback spoken by the patient 11 into the remote client 18 is processed into a quality of life measures set 228 (block 240), as further described below with reference to FIG. 17. The voice feedback is spoken substantially contemporaneous to the collection of an identified device measures set 50. The appropriate collected device measures set 50 can be matched to and identified with (not shown) the quality of life measures set 228 either by matching their respective dates and times of day or by similar means, either by the remote client 18 or the server system 16. The quality of life measures set 228 and the identified collected measures set 50 are sent over the internetwork 15 to the server system 16 (block 241). Note the quality of life measures set 228 and the identified collected measures set 50 both need not be sent over the internetwork 15 at the same time, so long as the two sets are ultimately paired based on, for example, date and time of day. The quality of life measures set 228 and the identified collected measures set 50 are received by the server system 16 (block 242) and stored in the appropriate patient care record in the database 52 (block 243). Finally, the quality of life measures set 228, identified collected measures set 50, and one or more collected measures sets 50 are analyzed (block 244) and feedback, including a patient status indicator 54 (shown in FIG. 14), is provided to the patient (block 245).

Figure 17:
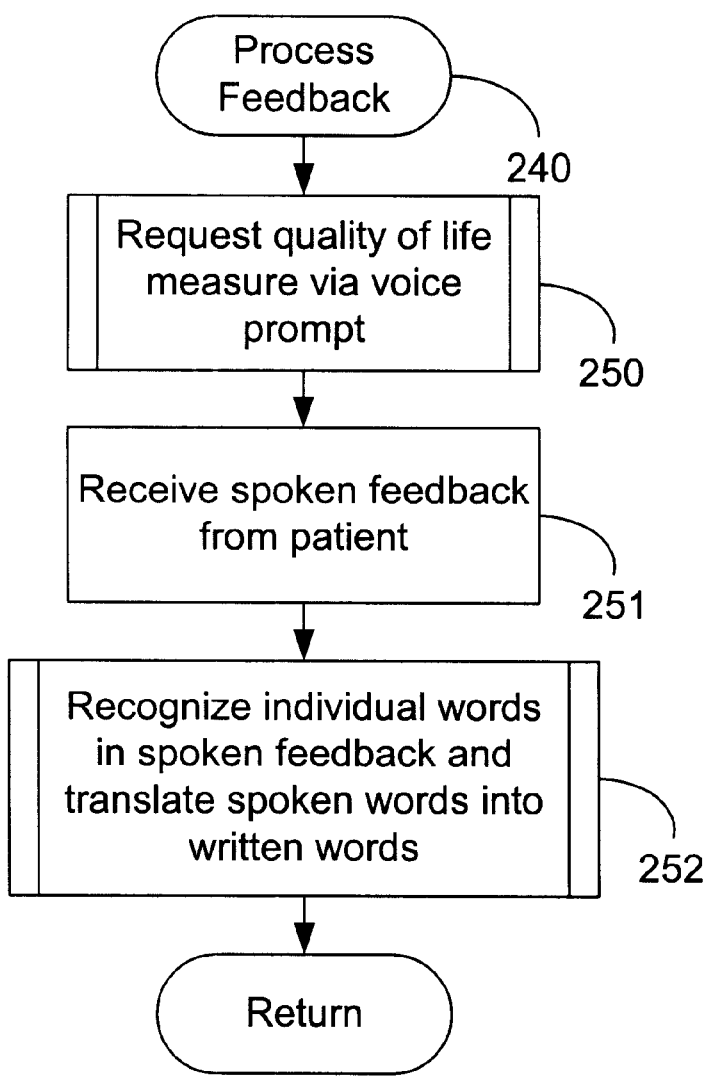
FIG. 17 is a flow diagram showing a routine for processing voice feedback for use in the method of FIGS. 16A–16B.

FIG. 17 is a flow diagram showing the routine for processing voice feedback 240 for use in the method of FIGS. 16A–16B. The purpose of this routine is to facilitate a voice interactive session with the patient 11 during which is developed a normalized set of quality of life measures. Thus, the remote client 18 requests a quality of life measure via a voice prompt (block 250), played on the speaker 202 (shown in FIG. 13), as further described below with reference to FIG. 18. The remote client 18 receives the spoken feedback from the patient 11 (block 251) via the microphone 201 (shown in FIG. 13). The remote client 18 recognizes individual words in the spoken feedback and translates those words into written words (block 252), as further described below with reference to FIG. 19. The routine returns at the end of the voice interactive session.

Figure 18:
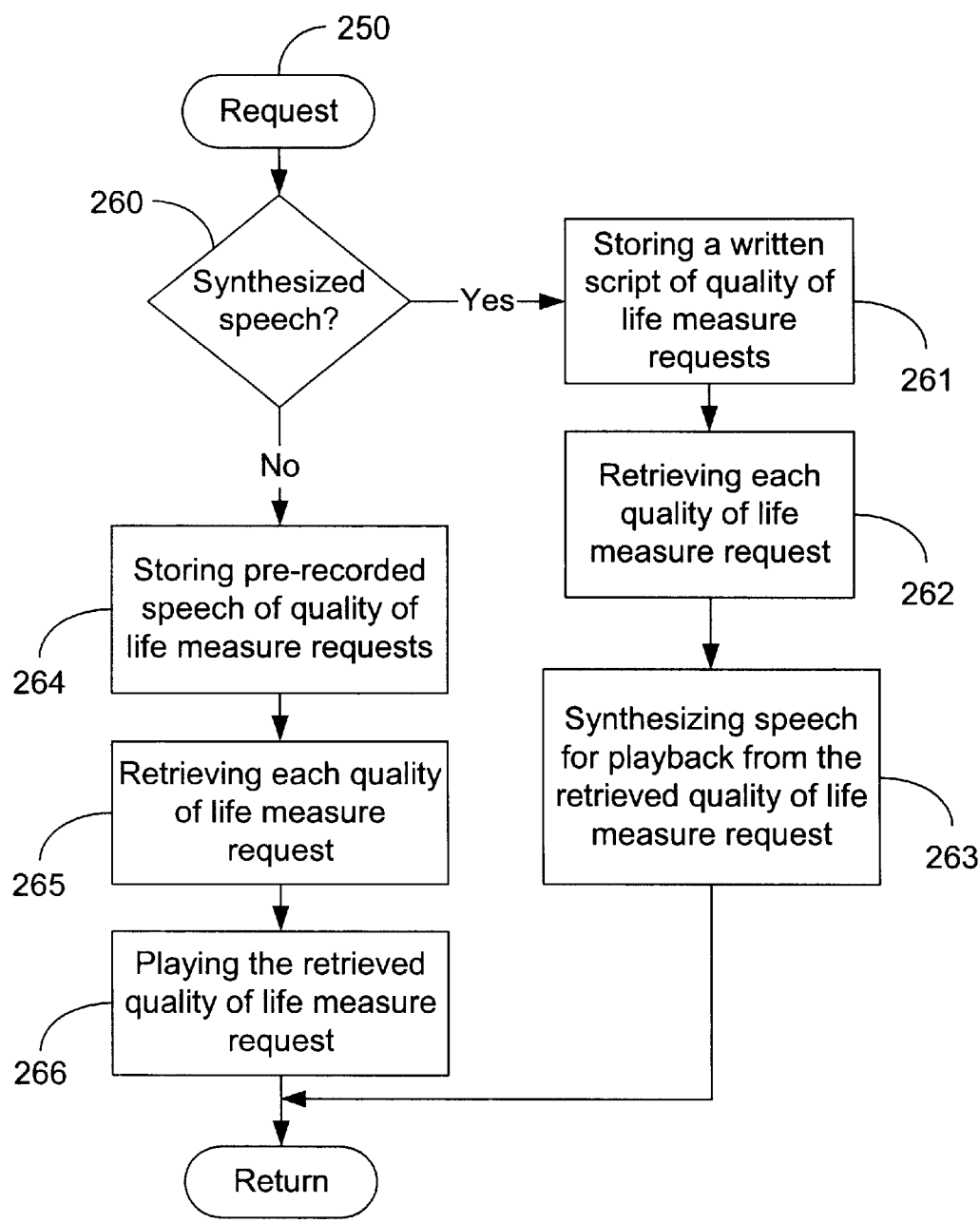
FIG. 18 is a flow diagram showing a routine for requesting a quality of life measure for use in the routine of FIG. 17.

FIG. 18 is a flow diagram showing the routine for requesting a quality of life measure 251 for use in the routine 240 of FIG. 17. The purpose of this routine is to present a voice prompt 226 to the user via the speaker 202. Either pre-recorded speech 221 or speech synthesized from a written script 220 can be used. Thus, if synthesized speech is employed by the remote client 18 (block 260), a written script, such as a voice markup language script, specifying questions and phrases which with to request quality of life measures is stored (block 261) on the secondary storage 219 of the remote client 18. Each written quality of life measure request is retrieved by the remote client 18 (block 262) and synthesized into speech for playback to the patient 11 (block 263). Alternatively, if pre-recorded speech is employed by the remote client 18 (block 260), pre-recorded voice "bites" are stored (block 264) on the secondary storage 219 of the remote client 18. Each pre-recorded quality of life measure request is retrieved by the remote client 18 (block 265) and played back to the patient 11 (block 266). The routine then returns.

Figure 19:
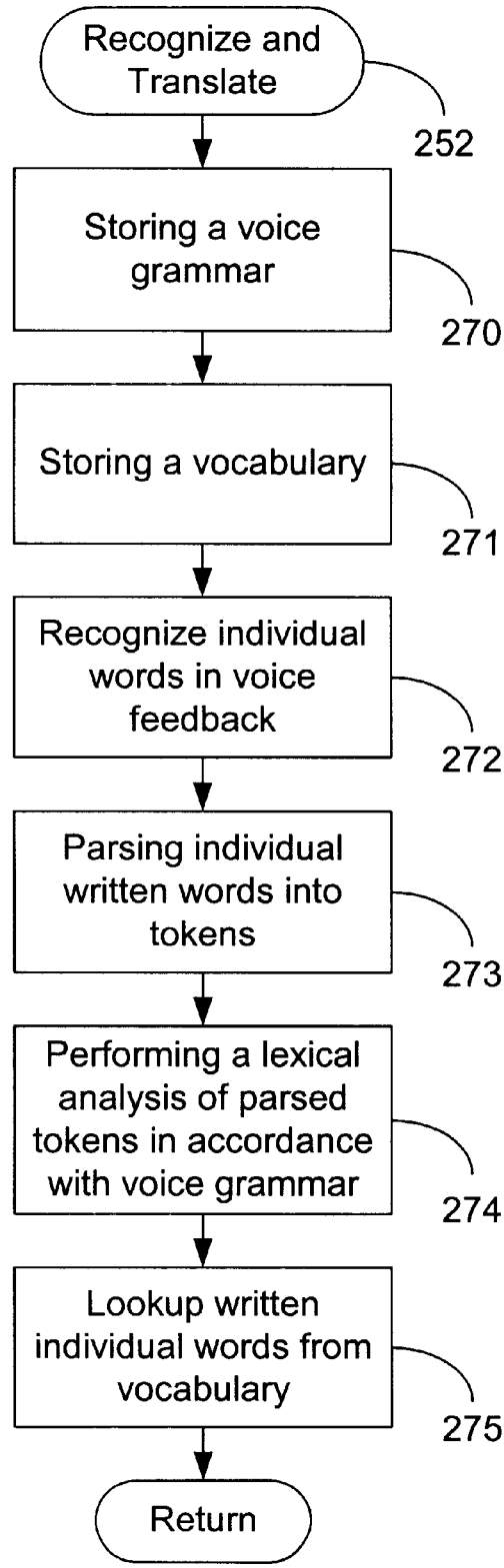
FIG. 19 is a flow diagram showing a routine for recognizing and translating individual spoken words for use in the routine of FIG. 17.

FIG. 19 is a flow diagram showing the routine for recognizing and translating individual spoken words 252 for use in the routine 240 of FIG. 17. The purpose of this routine is to receive and interpret a free-form voice response 227 from the user via the microphone 201. First, a voice grammar consisting of a lexical structuring of words, phrases, and sentences is stored (block 270) on the secondary storage 219 of the remote client 18. Similarly, a vocabulary of individual words and their commonly accepted synonyms is stored (block 271) on the secondary storage 219 of the remote client 18. After individual words in the voice feedback are recognized (block 272), the individual words are parsed into tokens (block 273). The voice feedback is then lexically analyzed using the tokens and in accordance with the voice grammar 222 (block 274) to determine the meaning of the voice feedback. If necessary, the vocabulary 223 is referenced to lookup synonyms of the individual words (block 275). The routine then returns.

Figure 20:
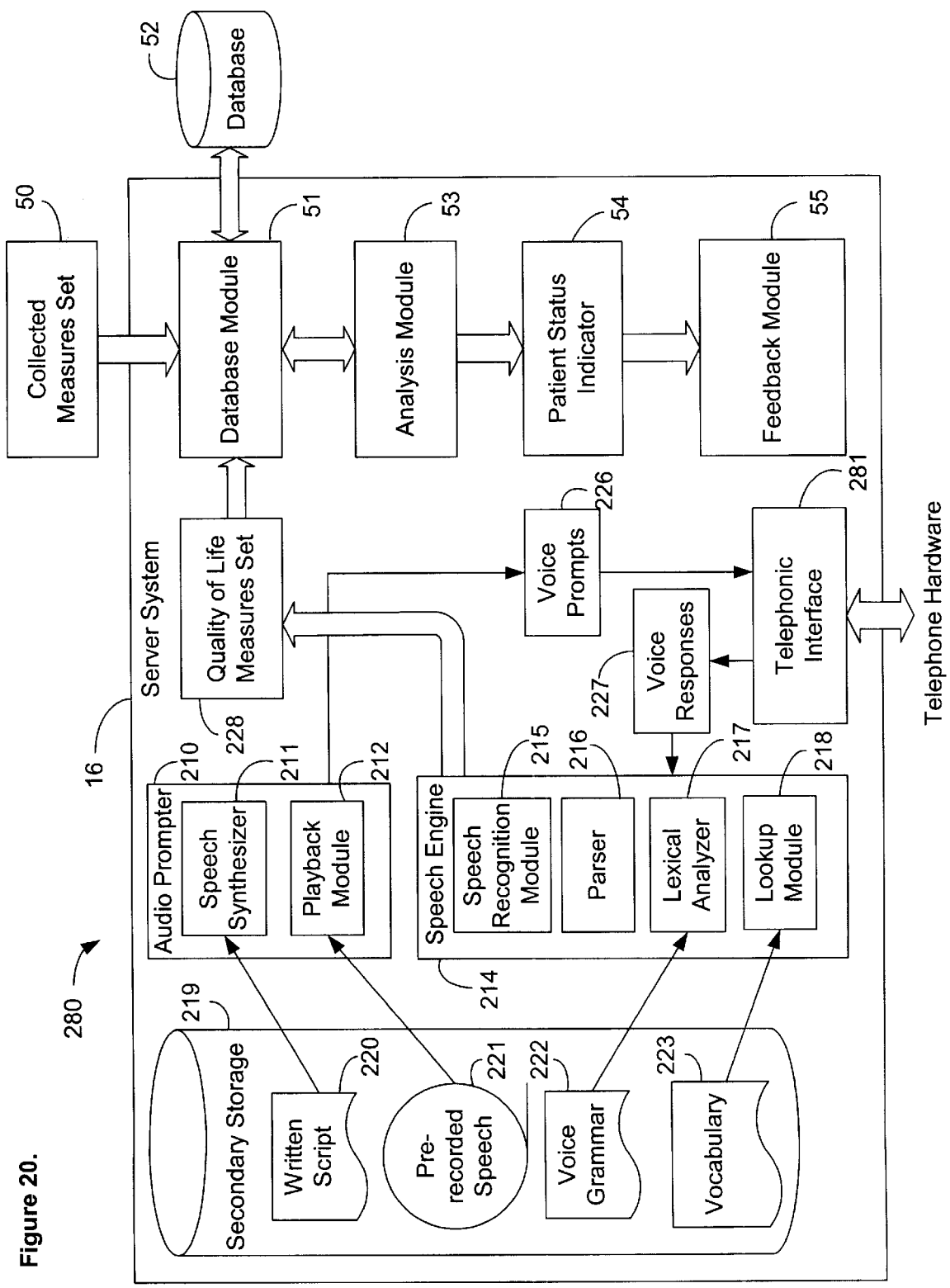
FIG. 20 is a block diagram showing the software modules of the server system in a further embodiment of the system of FIG. 12.

FIG. 20 is a block diagram showing the software modules of the server system in a further embodiment of the system 200 of FIG. 12. The functionality of the remote client 18 in providing normalized voice feedback is incorporated directly into the server system 16. The system 200 of FIG. 12 requires the patient 11 to provide spoken feedback via a locally situated remote client 18. However, the system 280 enables a patient 11 to alternatively provide spoken feedback via a telephone network 203 using a standard telephone 203, including a conventional wired telephone or a wireless telephone, such as a cellular telephone. The server system 16 is augmented to include the audio prompter 210, the speech engine 214, and the data stored in the secondary storage 219. A telephonic interface 280 interfaces the server system 16 to the telephone network 203 and receives voice responses 227 and sends voice prompts 226 to and from the server system 16. Telephonic interfacing devices are commonly known in the art.

Figure 21:
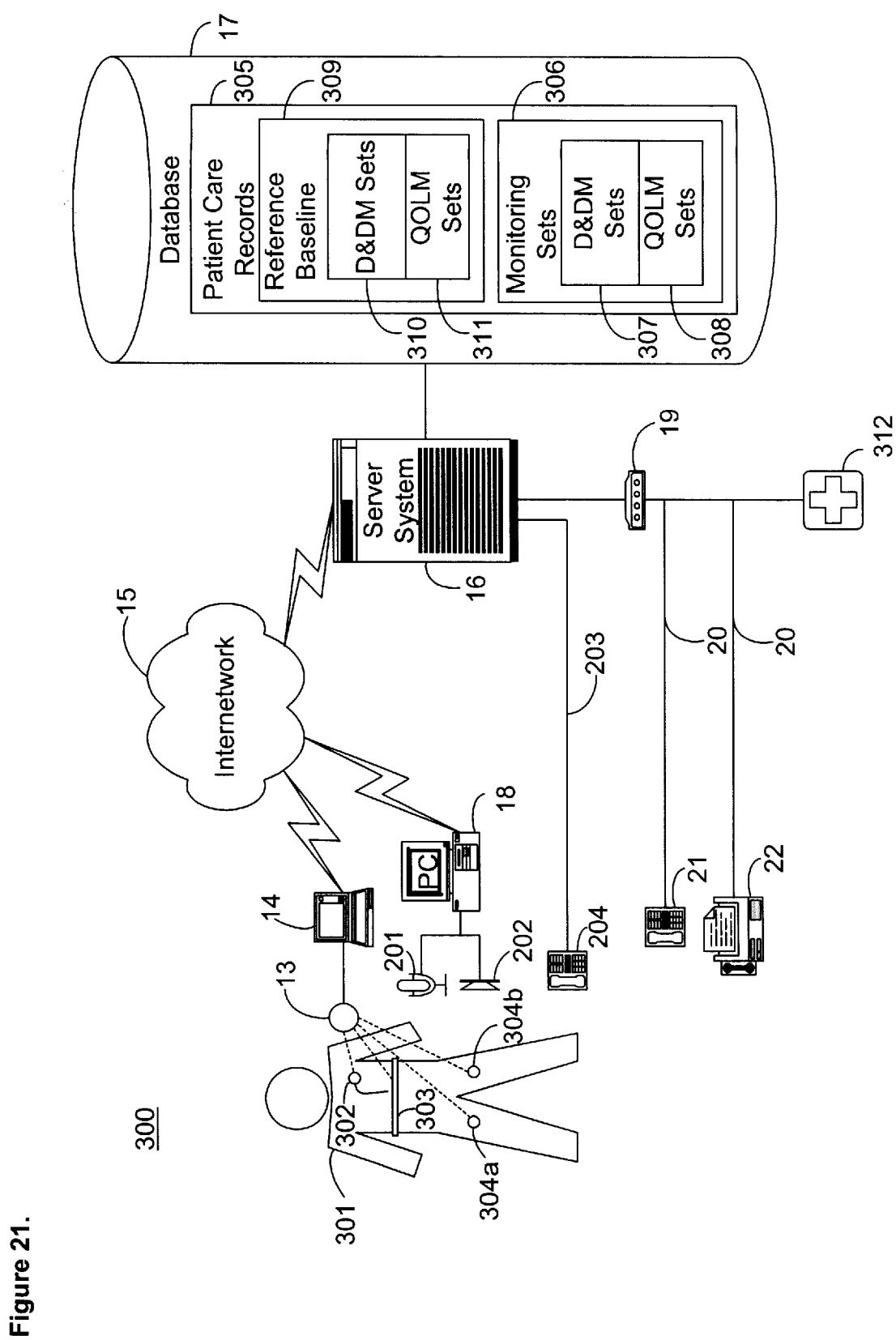
FIG. 21 is a block diagram showing a system for providing normalized voice feedback from an individual patient in an automated collection and analysis patient care system in accordance with a further embodiment of the present invention.

FIG. 21 is a block diagram showing a system for providing normalized voice feedback from an individual patient in an automated collection and analysis patient care system 300 in accordance with a further embodiment of the present invention. The system 300 provides remote patient care in a manner similar to the system 200 of FIG. 12, but with additional functionality for diagnosing and monitoring multiple sites within a patient's body using a variety of patient sensors for diagnosing one or more disorder. The patient 301 can be the recipient of an implantable medical device 302, as described above, or have an external medical device 303 attached, such as a Holter monitor-like device for monitoring electrocardiograms. In addition, one or more sites in or around the patient's body can be monitored using multiple sensors 304a, 304b, such as described in U.S. Pat. Nos. 4,987,897; 5,040,536; 5,113,859; and 5,987,352, the disclosures of which are incorporated herein by reference. One automated system and method for collecting and analyzing retrieved patient information suitable for use with the present invention is described in the related, commonly-owned U.S. patent application, Ser. No. 09/476,602, entitled "System And Method For Automated Collection And Analysis Of Regularly Retrieved Patient Information For Remote Patient Care," pending, filed Dec. 31, 1999, the disclosure of which is incorporated herein by reference. Other types of devices with physiological measure sensors, both heterogeneous and homogenous, could be used, either within the same device or working in conjunction with each other, as is known in the art.

As part of the system 300, the database 17 stores patient care records 305 for each individual patient to whom remote patient care is being provided. Each patient care record 305 contains normal patient identification and treatment profile information, as well as medical history, medications taken, height and weight, and other pertinent data (not shown). The patient care records 305 consist primarily of monitoring sets 306 storing device and derived measures (D&DM) sets 307 and quality of life and symptom measures (QOLM) sets 308 recorded and determined thereafter on a regular, continuous basis. The organization of the device and derived measures sets 305 for an exemplary cardiac patient care record is described above with reference to FIG. 5. The organization of the quality of life and symptom measures sets 308 is further described below with reference to FIG. 23.

Optionally, the patient care records 305 can further include a reference baseline 309 storing a special set of device and derived reference measures sets 310 and quality of life and symptom measures sets 311 recorded and determined during an initial observation period, such as described in the related, commonly-owned U.S. patent application, Ser. No. 09/476,601, entitled "System And Method For Determining A Reference Baseline Of Individual Patient Status For Use In An Automated Collection And Analysis Patient Care System," pending, filed Dec. 31, 1999, the disclosure of which is incorporated herein by reference. Other forms of database organization are feasible.

Finally, simultaneous notifications can also be delivered to the patient's physician, hospital, or emergency medical services provider 312 using feedback means similar to that used to notify the patient. As described above, the feedback could be by electronic mail or by automated voice mail or facsimile. Furthermore, the spoken voice feedback from the patient and the feedback provided by the system 200 can be communicated by means of or in combination with the medical device itself, whether implantable, external or otherwise.

Figure 22:
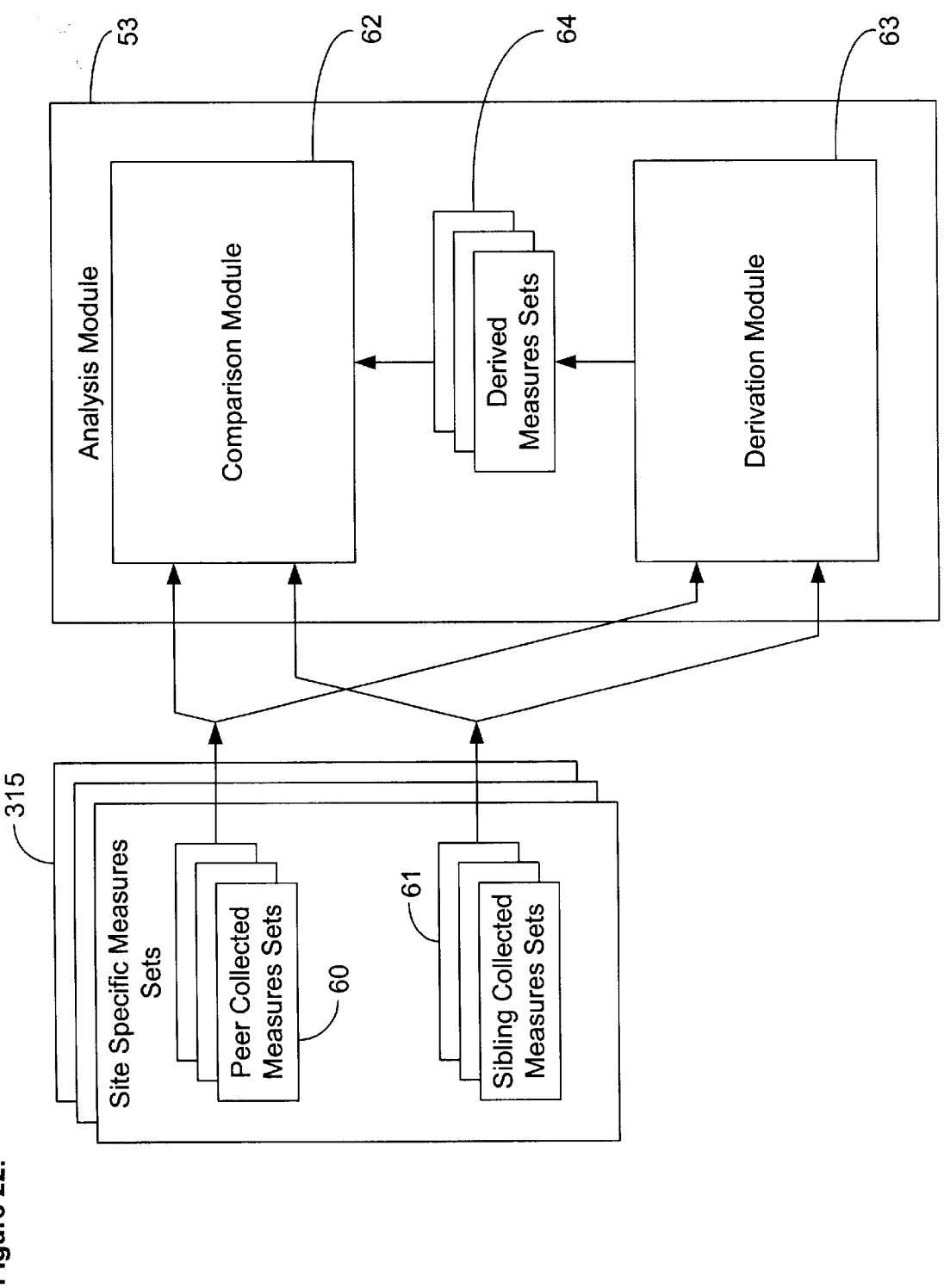
FIG. 22 is a block diagram showing the analysis module of the server system of FIG. 21.

FIG. 22 is a block diagram showing the analysis module 53 of the server system 16 of FIG. 21. The peer collected measures sets 60 and sibling collected measures sets 61 can be organized into site specific groupings based on the sensor from which they originate, that is, implantable medical device 302, external medical device 303, or multiple sensors 304a, 304b. The functionality of the analysis module 53 is augmented to iterate through a plurality of site specific measures sets 315 and one or more disorders.

As described above, as an adjunct to remote patient care through the monitoring of measured physiological data via implantable medical device 302, external medical device 303 and multiple sensors 304a, 304b, quality of life and symptom measures sets 308 can also be stored in the database 17 as part of the monitoring sets 306. A quality of life measure is a semi-quantitative self-assessment of an individual patient's physical and emotional well-being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16.

Figure 23:
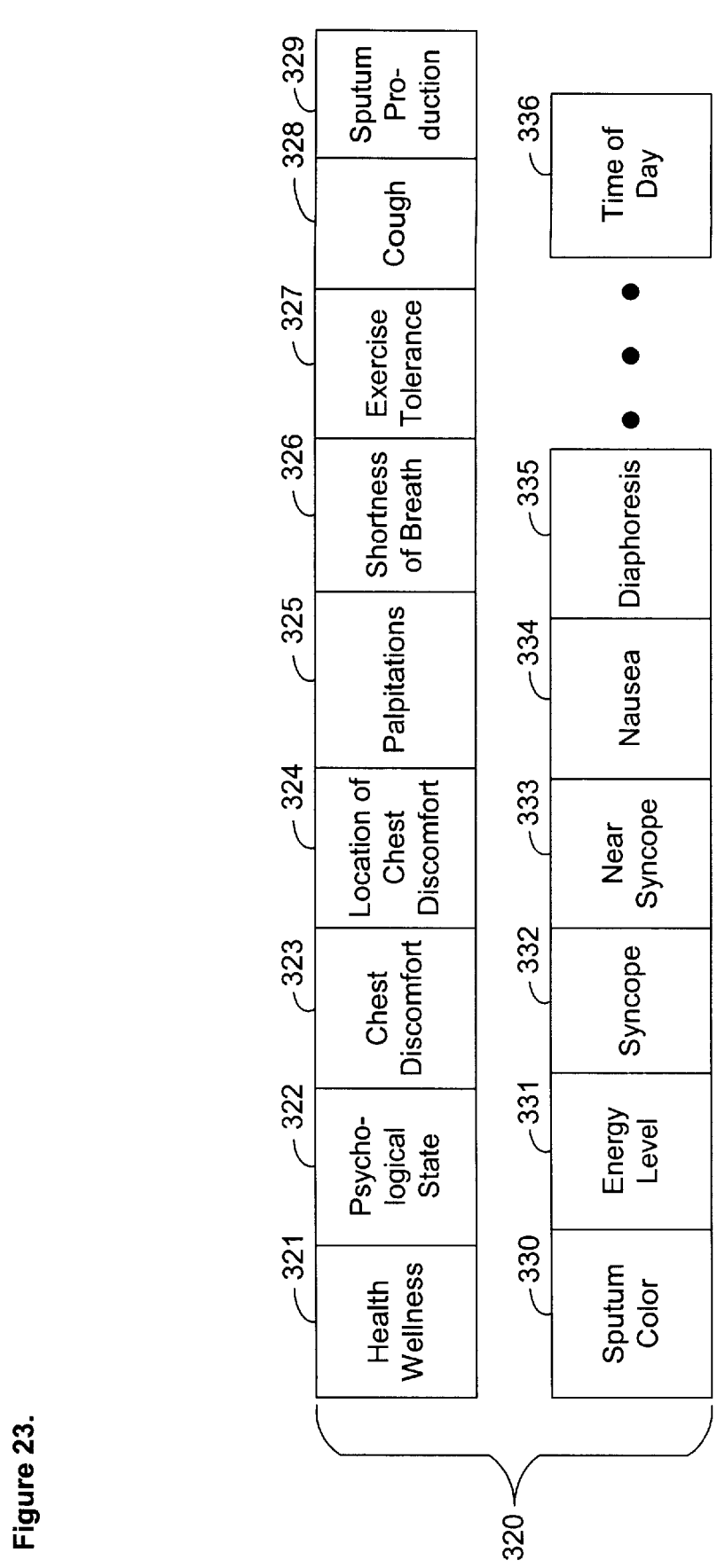
FIG. 23 is a database schema showing, by way of example, the organization of a quality of life and symptom measures set record for care of patients stored as part of a patient care record in the database of the system of FIG. 21.

FIG. 23 is a database schema which augments the database schema described above with reference to FIG. 15 and showing, by way of example, the organization of a quality of life and symptom measures set record 320 for care of patients stored as part of a patient care record 305 in the database 17 of the system 300 of FIG. 21. The following exemplary information is recorded for a patient: overall health wellness 321, psychological state 322, chest discomfort 323, location of chest discomfort 324, palpitations 325, shortness of breath 326, exercise tolerance 327, cough 328, sputum production 329, sputum color 330, energy level 331, syncope 332, near syncope 333, nausea 334, diaphoresis 335, time of day 91, and other quality of life and symptom measures as would be known to one skilled in the art.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452–454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 307 and the symptoms during the six-minute walk to quality of life and symptom measures sets 308.

FIG. 24 is a record view showing, by way of example, a set of partial cardiac patient care records stored in the database 17 of the system 300 of FIG. 21. Three patient care records are again shown for Patient 1, Patient 2, and Patient 3 with each of these records containing site specific measures sets 315, grouped as follows. First, the patient care record for Patient 1 includes three site specific measures sets A, B and C, corresponding to three sites on Patient 1's body. Similarly, the patient care record for Patient 2 includes two site specific measures sets A and B, corresponding to two sites, both of which are in the same relative positions on Patient 2's body as the sites for Patient 1. Finally, the patient care record for Patient 3 includes two site specific measures sets A and D, also corresponding to two medical device sensors, only one of which, Site A, is in the same relative position as Site A for Patient 1 and Patient 2.

The analysis module 53 (shown in FIG. 22) performs two further forms of comparison in addition to comparing the individual measures for a given patient to other individual measures for that same patient or to other individual measures for a group of other patients sharing the same disease-specific characteristics or to the patient population in general. First, the individual measures corresponding to each body site for an individual patient can be compared to other individual measures for that same patient, a peer group or a general patient population. Again, these comparisons might be peer-to-peer measures projected over time, for instance, comparing measures for each site, A, B and C, for Patient 1, $X_{n_A}, X_{n'_A}, X_{n''_A}, X_{n-1_A}, X_{n-1'_A}, X_{n-1''_A}, X_{n-2_A}, X_{n-2'_A}, X_{n-2''_A} \ldots X_{0_A}, X_{0'_A}, X_{0''_A}; X_{n_B}, X_{n'_B}, X_{n''_B}, X_{n-1_B}, X_{n-1'_B}, X_{n-1''_B}, X_{n-2_B}, X_{n-2'_B}, X_{n-2''_B} \ldots X_{0_B}, X_{0'_B}, X_{0''_B}; X_{n_C}, X_{n'_C}, X_{n''_C}, X_{n-1_C}, X_{n-1'_C}, X_{n-1''_C}, X_{n-2_C}, X_{n-2'_C}, X_{n-2''_C} \ldots X_{0_C}, X_{0'_C}, X_{0''_C}$; comparing comparable measures for Site A for the three patients, $X_{n_A}, X_{n'_A}, X_{n''_A}, X_{n-1_A}, X_{n-1'_A}, X_{n-1''_A}, X_{n-2_A}, X_{n-2'_A}, X_{n-2''_A} \ldots X_{0_A}, X_{0'_A}, X_{0''_A}$; or comparing the individual patient's measures to an average from the group. Similarly, these comparisons might be sibling-to-sibling measures for single snapshots, for instance, comparing comparable measures for Site A for the three patients, $X_{n_A}, X_{n'_A}, X_{n''_A}, Y_{n_A}, Y_{n'_A}, Y_{n''_A}$, and $Z_{n_A}, Z_{n'_A}, Z_{n''_A}$, or comparing those same comparable measures for Site A projected over time, for instance, $X_{n_A}, X_{n'_A}, X_{n''_A}, Y_{n_A}, Y_{n'_A}, Y_{n''_A}, Z_{n_A}, Z_{n'_A}, Z_{n''_A}, X_{n-1_A}, X_{n-1'_A}, X_{n-1''_A}, Y_{n-1_A}, Y_{n-1'_A}, Y_{n-1''_A}, Z_{n-1_A}, Z_{n-1'_A}, Z_{n-1''_A}, X_{n-2_A}, X_{n-2'_A}, X_{n-2''_A}, Y_{n-2_A}, Y_{n-2'_A}, Y_{n-2''_A}, Z_{n-2_A}, Z_{n-2'_A}, Z_{n-2''_A} \ldots X_{0_A}, X_{0'_A}, X_{0''_A}, Y_{0_A}, Y_{0'_A}, Y_{0''_A}$, and $Z_{0_A}, Z_{0'_A}, Z_{0''_A}$. Other forms of site-specific comparisons, including comparisons between individual measures from non-comparable sites between patients, are feasible.

Second, the individual measures can be compared on a disorder specific basis. The individual measures stored in each cardiac patient record can be logically grouped into measures relating to specific disorders and diseases, for instance, congestive heart failure, myocardial infarction, respiratory distress, and atrial fibrillation. The foregoing comparison operations performed by the analysis module 53 are further described below with reference to FIGS. 26A–26B.

Figure 25:
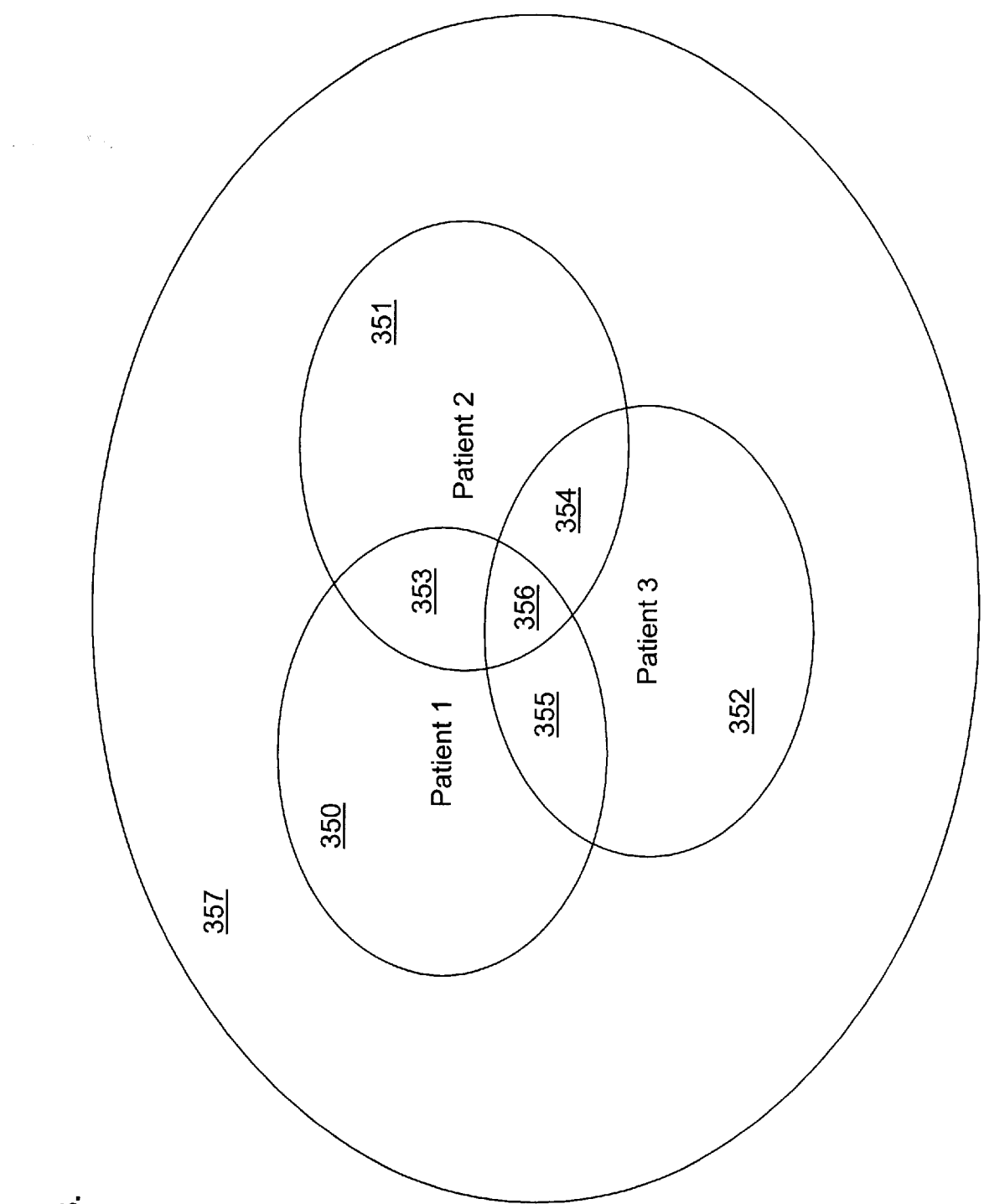
FIG. 25 is a Venn diagram showing, by way of example, peer group overlap between the partial patient care records of FIG. 24.

FIG. 25 is a Venn diagram showing, by way of example, peer group overlap between the partial patient care records 305 of FIG. 24. Each patient care record 305 includes characteristics data 350, 351, 352, including personal traits, demographics, medical history, and related personal data, for patients 1, 2 and 3, respectively. For example, the characteristics data 350 for patient 1 might include personal traits which include gender and age, such as male and an age between 40–45; a demographic of resident of New York City; and a medical history consisting of anterior myocardial infraction, congestive heart failure and diabetes. Similarly, the characteristics data 351 for patient 2 might include identical personal traits, thereby resulting in partial overlap 353 of characteristics data 350 and 351. Similar characteristics overlap 354, 355, 356 can exist between each respective patient. The overall patient population 357 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 356 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

Figure 26A:
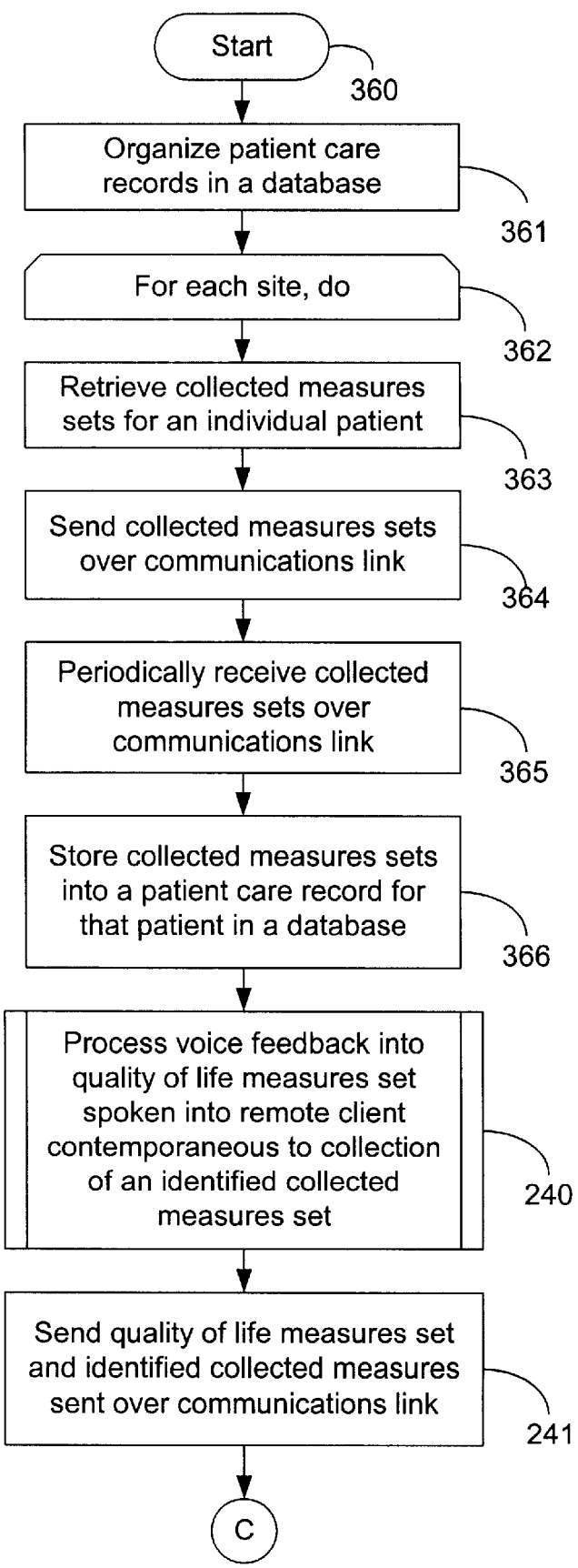
FIGS. 26A–26B are flow diagrams showing a method for providing normalized voice feedback from an individual patient in an automated collection and analysis patient care system in accordance with a further embodiment of the present invention.
Figure 26B:
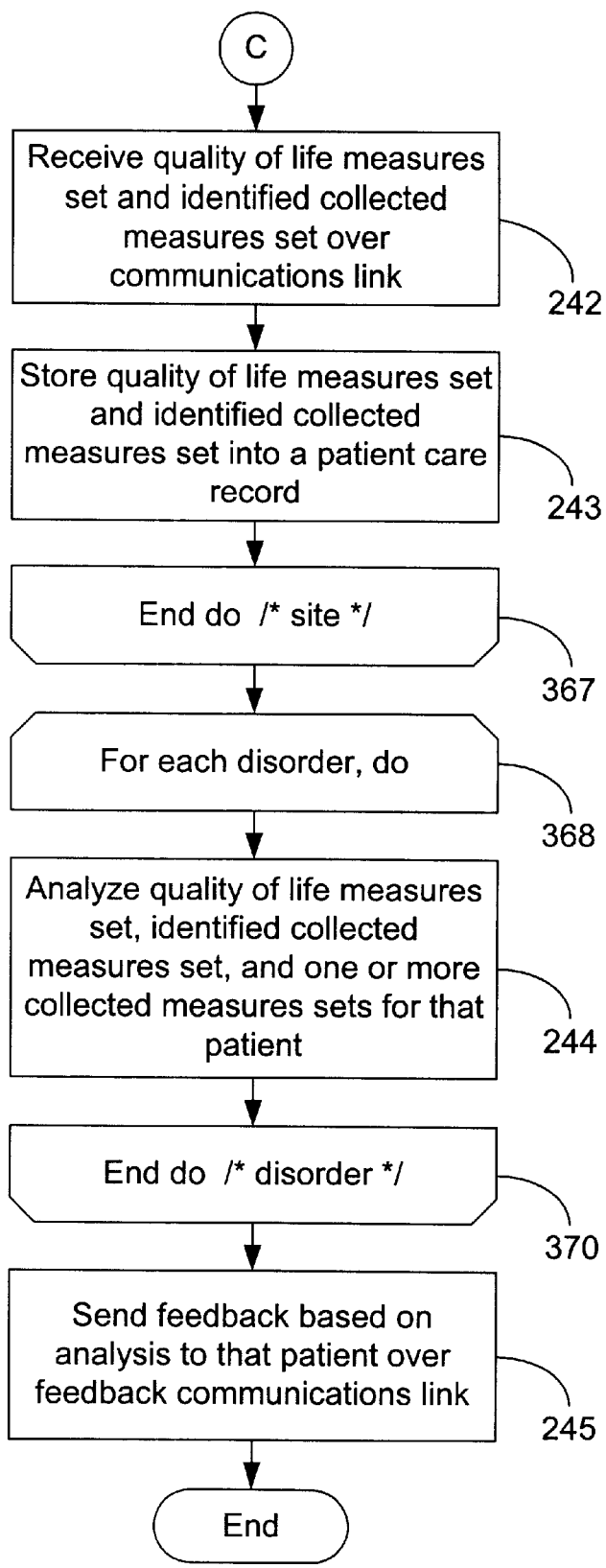

FIGS. 26A–26B are flow diagrams showing a method for providing normalized voice feedback from an individual patient in an automated collection and analysis patient care system 360 in accordance with a further embodiment of the present invention. As with the method 239 of FIGS. 16A and 16B, this method is also implemented as a conventional computer program and performs the same set of steps as described with reference to FIGS. 16A and 16B with the following additional functionality. As before, the patient care records are organized in the database 17 with a unique patient care record assigned to each individual patient (block 361). Next, the individual measures for each site are iteratively obtained in a first processing loop (blocks 362–367) and each disorder is iteratively analyzed in a second processing loop (blocks 368–370). Other forms of flow control are feasible, including recursive processing.

During each iteration of the first processing loop (blocks 362–367), the collected measures sets for an individual patient are retrieved from the medical device or sensor located at the current site (block 363) using a programmer, interrogator, telemetered signals transceiver, and the like. The retrieved collected measures sets are sent, on a substantially regular basis, over the internetwork 15 or similar communications link (block 364) and periodically received by the server system 16 (block 365). The collected measures sets are stored into the patient care record 305 in the database 17 for that individual patient (block 366). Any voice feedback spoken by the patient 11 into the remote client 18 is processed into a quality of life measures set 228 (block 240), as described above with reference to FIG. 17. The voice feedback is spoken substantially contemporaneous to the collection of an identified device measures set 50. The appropriate collected device measures set 50 can be matched to and identified with (not shown) the quality of life measures set 228 either by matching their respective dates and times of day or by similar means, either by the remote client 18 or the server system 16. The quality of life measures set 228 and the identified collected measures set 50 are sent over the internetwork 15 to the server system 16 (block 241). The quality of life measures set 228 and the identified collected measures set 50 are received by the server system 16 (block 242) and stored in the appropriate patient care record in the database 52 (block 243).

During each iteration of the second processing loop (blocks 368–370), the quality of life measures set 228, identified collected measures set 50, and one or more of the collected measures sets for that patient are analyzed for the current disorder are analyzed (block 244). Finally, feedback based on the analysis is sent to that patient over the internetwork 15 as an email message, via telephone line as an automated voice mail or facsimile message, or by similar feedback communications link (block 245). In addition, the measures sets can be further evaluated and matched to diagnose specific medical disorders, such as congestive heart failure, myocardial infarction, respiratory distress, and atrial fibrillation, as described in related, commonly-owned U.S. patent applications, Ser. No. 09/441,623, pending, filed Nov. 16, 1999; Ser. No. 09/441,612, pending, filed Nov. 16, 1999; Ser. No. 09/442, 125, pending, filed Nov. 16, 1999; and Ser. No. 09/441,613, pending, filed Nov. 16, 1999, the disclosures of which are incorporated herein by reference. In addition, multiple near-simultaneous disorders can be ordered and prioritized as part of the patient status indicator as described in the related, commonly-owned U.S. patent application Ser. No. 09/441,405, pending, filed Nov. 16, 1999, the disclosure of which is incorporated herein by reference.

Therefore, through the use of the collected measures sets, the present invention makes possible immediate access to expert medical care at any time and in any place. For example, after establishing and registering for each patient an appropriate baseline set of measures, the database server could contain a virtually up-to-date patient history, which is available to medical providers for the remote diagnosis and prevention of serious illness regardless of the relative location of the patient or time of day.

Moreover, the gathering and storage of multiple sets of critical patient information obtained on a routine basis makes possible treatment methodologies based on an algorithmic analysis of the collected data sets. Each successive introduction of a new collected measures set into the database server would help to continually improve the accuracy and effectiveness of the algorithms used. In addition, the present invention potentially enables the detection, prevention, and cure of previously unknown forms of disorders based on a trends analysis and by a cross-referencing approach to create continuously improving peer-group reference databases.

Similarly, the present invention makes possible the provision of tiered patient feedback based on the automated analysis of the collected measures sets. This type of feedback system is suitable for use in, for example, a subscription based health care service. At a basic level, informational feedback can be provided by way of a simple interpretation of the collected data. The feedback could be built up to provide a gradated response to the patient, for example, to notify the patient that he or she is trending into a potential trouble zone. Human interaction could be introduced, both by remotely situated and local medical practitioners. Finally, the feedback could include direct interventive measures, such as remotely reprogramming a patient's IPG.

Finally, the present invention allows "live" patient voice feedback to be captured simultaneously with the collection of physiological measures by their implantable medical device. The voice feedback is normalized to a standardized set of quality of life measures which can be analyzed in a remote, automated fashion. The voice feedback could also be coupled with visual feedback, such as through digital photography or video, to provide a more complete picture of the patient's physical well-being.

While the invention has been particularly shown and described as referenced to the embodiments thereof, those skilled in the art will understand that the foregoing and other changes in form and detail may be made therein without departing from the spirit and scope of the invention.

What is claimed is:

1. A system for providing normalized voice feedback from an individual patient in an automated collection and analysis patient care system, comprising:
   a medical device having a sensor for monitoring at least one physiological measure of an individual patient, the collected measures set comprising individual measures which each relate to patient information recorded by the medical device;
   a remote client processing voice feedback into a set of quality of life measures which each relate to patient self-assessment indicators, the voice feedback having been spoken by the individual patient into a remote client substantially contemporaneous to the collection of an identifiable device measures set;
   a network server over which is periodically received a set of collected measures retrieved on a substantially regular basis from the medical device, the identified collected device measures set is received from the medical device, and the quality of life measures set is received from the remote client;
   a database coupled to the network server and storing the collected measures set, the identified collected device measures set and the quality of life measures set into a patient care record for the individual patient within a database organized to store one or more patient care records which each comprise a plurality of the collected measures sets; and
   an application server coupled to the database and analyzing the identified collected device measures set, the quality of life measures set, and one or more of the collected device measures sets in the patient care record for the individual patient relative to one or more other collected device measures sets stored in the database to determine a patient status indicator.

2. A system according to claim 1, further comprising:
   the network server repeatedly receiving one or more collected measures sets which are each recorded by a sensor which monitors at least one physiological measure of the individual patient, each such sensor monitoring a site within the individual patient unique from the site monitored by any other such sensor;
   the database storing each collected measures set organized by specific site into the patient care record for the individual patient within the database; and
   the application server analyzing one or more of the site specific collected measures sets in the patient care record for each site within the individual patient relative to one or more other site specific collected measures sets stored in the database to determine a patient status indicator.

3. A system according to claim 2, wherein the one or more site specific collected measures sets and the one or more other site specific collected measures sets both store measures collected from the same relative site.

4. A system according to claim 2, wherein the one or more site specific collected measures sets and the one or more other site specific collected measures sets both store measures collected from a different site.

5. A system according to claim 1, the remote client further comprising:
   an audio prompter requesting a quality of life measure via a voice prompt played on the remote client to the individual patient.

6. A system according to claim 5, further comprising:
   a written script comprising a plurality of quality of life measure requests stored within the remote client; and
   the audio prompter further comprising a speech synthesizer module retrieving each quality of life request from the stored written script with each such retrieved quality of life measure request comprising one such voice prompt and synthesizing speech for playback from the retrieved quality of life request.

7. A system according to claim 5, further comprising:
pre-recorded speech comprising a plurality of quality of life measure requests stored within the remote client; and the audio prompter further comprising a playback module retrieving each quality of life request from the stored pre-recorded speech with each such retrieved quality of life measure request comprising one such voice prompt and playing the pre-recorded speech from the retrieved quality of life request.

8. A system according to claim 1, the remote client further comprising:
a speech engine recognizing individual words in the spoken voice feedback and translating the individual spoken words into written individual words.

9. A system according to claim 8, further comprising:
a voice grammar stored within the remote client, the voice grammar comprising a plurality of speech phrases expressed in a natural language, each speech phrase corresponding to a normalized quality of life measure;

the speech engine further comprising:
a parser parsing the written individual words into tokens; and
a lexical analyzer performing a lexical analysis of the parsed tokens in accordance with the voice grammar to identify one such normalized quality of life measure.

10. A system according to claim 8, further comprising:
a vocabulary stored within the remote client, the vocabulary comprising the written individual words; and
the speech engine further comprising a lookup module performing a lookup of the written individual words from the vocabulary stored within the remote client.

11. A system according to claim 1, the remote client further comprising:
wherein the remote client comprises at least one of a personal computer, an audio interface, and a telephony instrument.

12. A method for providing normalized voice feedback from an individual patient in an automated collection and analysis patient care system, comprising:
periodically receiving a set of collected measures retrieved on a substantially regular basis from a medical device having a sensor for monitoring at least one physiological measure of an individual patient, the collected measures set comprising individual measures which each relate to patient information recorded by the medical device;
storing the collected measures set into a patient care record for the individual patient within a database organized to store one or more patient care records which each comprise a plurality of the collected measures sets;
processing voice feedback into a set of quality of life measures which each relate to patient self-assessment indicators, the voice feedback having been spoken by the individual patient into a remote client substantially contemporaneous to the collection of an identifiable device measures set;
receiving the identified collected device measures set and the quality of life measures set;
storing the identified collected device measures set and the quality of life measures set into the patient care record for the individual patient within the database; and analyzing the identified collected device measures set, the quality of life measures set, and one or more of the collected device measures sets in the patient care record for the individual patient relative to one or more other collected device measures sets stored in the database to determine a patient status indicator.

13. A method according to claim 12, further comprising:
repeatedly receiving one or more collected measures sets which are each recorded by a sensor which monitors at least one physiological measure of the individual patient, each such sensor monitoring a site within the individual patient unique from the site monitored by any other such sensor,
storing each collected measures set organized by specific site into the patient care record for the individual patient within the database; and
analyzing one or more of the site specific collected measures sets in the patient care record for each site within the individual patient relative to one or more other site specific collected measures sets stored in the database to determine a patient status indicator.

14. A method according to claim 13, wherein the one or more site specific collected measures sets and the one or more other site specific collected measures sets both store measures collected from the same relative site.

15. A method according to claim 13, wherein the one or more site specific collected measures sets and the one or more other site specific collected measures sets both store measures collected from a different site.

16. A method according to claim 12, the operation of processing voice feedback further comprising:
requesting a quality of life measure via a voice prompt played on the remote client to the individual patient.

17. A method according to claim 16, the operation of requesting a quality of life measure further comprising:
storing a written script comprising a plurality of quality of life measure requests within the remote client;
retrieving each quality of life request from the stored written script with each such retrieved quality of life measure request comprising one such voice prompt; and
synthesizing speech for playback from the retrieved quality of life request.

18. A method according to claim 16, the operation of requesting a quality of life measure further comprising:
storing pre-recorded speech comprising a plurality of quality of life measure requests within the remote client;
retrieving each quality of life request from the stored pre-recorded speech with each such retrieved quality of life measure request comprising one such voice prompt; and
playing the pre-recorded speech from the retrieved quality of life request.

19. A method according to claim 12, the operation of processing voice feedback further comprising:
recognizing individual words in the spoken voice feedback; and
translating the individual spoken words into written individual words.

20. A method according to claim 19, further comprising:
storing a voice grammar within the remote client, the voice grammar comprising a plurality of speech phrases expressed in a natural language, each speech phrase corresponding to a normalized quality of life measure;

parsing the written individual words into tokens; and performing a lexical analysis of the parsed tokens in accordance with the voice grammar to identify one such normalized quality of life measure.

21. A method according to claim 19, further comprising:

storing the written individual words as a vocabulary within the remote client; and performing a lookup of the written individual words from the vocabulary stored within the remote client.

22. A method according to claim 12, wherein the remote client comprises at least one of a personal computer, an audio interface, and a telephony instrument.

23. A computer-readable storage medium holding code for providing normalized voice feedback from an individual patient in an automated collection and analysis patient care system, comprising:

periodically receiving a set of collected measures retrieved on a substantially regular basis from a medical device having a sensor for monitoring at least one physiological measure of an individual patient, the collected measures set comprising individual measures which each relate to patient information recorded by the medical device;

storing the collected measures set into a patient care record for the individual patient within a database organized to store one or more patient care records which each comprise a plurality of the collected measures sets;

processing voice feedback into a set of quality of life measures which each relate to patient self-assessment indicators, the voice feedback having been spoken by the individual patient into a remote client substantially contemporaneous to the collection of an identifiable device measures set;

receiving the identified collected device measures set and the quality of life measures set;

storing the identified collected device measures set and the quality of life measures set into the patient care record for the individual patient within the database; and analyzing the identified collected device measures set, the quality of life measures set, and one or more of the collected device measures sets in the patient care record for the individual patient relative to one or more other collected device measures sets stored in the database to determine a patient status indicator.

24. A storage medium according to claim 23, further comprising:

repeatedly receiving one or more collected measures sets which are each recorded by a sensor which monitors at least one physiological measure of the individual patient, each such sensor monitoring a site within the individual patient unique from the site monitored by any other such sensor;

storing each collected measures set organized by specific site into the patient care record for the individual patient within the database; and analyzing one or more of the site specific collected measures sets in the patient care record for each site within the individual patient relative to one or more other site specific collected measures sets stored in the database to determine a patient status indicator.

25. A storage medium according to claim 24, wherein the one or more site specific collected measures sets and the one or more other site specific collected measures sets both store measures collected from the same relative site.

26. A storage medium according to claim 24, wherein the one or more site specific collected measures sets and the one or more other site specific collected measures sets both store measures collected from a different site.

27. A storage medium according to claim 23, the operation of processing voice feedback further comprising:

requesting a quality of life measure via a voice prompt played on the remote client to the individual patient.

28. A storage medium according to claim 27, the operation of requesting a quality of life measure further comprising:

storing a written script comprising a plurality of quality of life measure requests within the remote client;

retrieving each quality of life request from the stored written script with each such retrieved quality of life measure request comprising one such voice prompt; and synthesizing speech for playback from the retrieved quality of life request.

29. A storage medium according to claim 27, the operation of requesting a quality of life measure further comprising:

storing pre-recorded speech comprising a plurality of quality of life measure requests within the remote client;

retrieving each quality of life request from the stored pre-recorded speech with each such retrieved quality of life measure request comprising one such voice prompt; and playing the pre-recorded speech from the retrieved quality of life request.

30. A storage medium according to claim 23, the operation of processing voice feedback further comprising:

recognizing individual words in the spoken voice feedback; and translating the individual spoken words into written individual words.

31. A storage medium according to claim 30, further comprising:

storing a voice grammar within the remote client, the voice grammar comprising a plurality of speech phrases expressed in a natural language, each speech phrase corresponding to a normalized quality of life measure;

parsing the written individual words into tokens; and performing a lexical analysis of the parsed tokens in accordance with the voice grammar to identify one such normalized quality of life measure.

32. A storage medium according to claim 30, further comprising:

storing the written individual words as a vocabulary within the remote client; and performing a lookup of the written individual words from the vocabulary stored within the remote client.

* * * * *

UNITED STATES PATENT AND TRADEMARK OFFICE
CERTIFICATE OF CORRECTION

PATENT NO. : 6,261,230 B1
DATED : July 17, 2001
INVENTOR(S) : Bardy

It is certified that error appears in the above-identified patent and that said Letters Patent is hereby corrected as shown below:

<u>Column 26,</u>
Line 13, "any other such sensor," should read -- any other such sensor; --.

Signed and Sealed this

Twentieth Day of August, 2002

*Attest:*

JAMES E. ROGAN
*Attesting Officer*     *Director of the United States Patent and Trademark Office*